US009745546B2

(12) United States Patent
Aviles et al.

(10) Patent No.: US 9,745,546 B2
(45) Date of Patent: Aug. 29, 2017

(54) CASSETTE FOR STERILITY TESTING

(71) Applicant: Rapid Micro Biosystems, Inc., Bedford, MA (US)

(72) Inventors: Robert C. Aviles, Merrimack, NH (US); Devin T. Michaud, Billerica, MA (US); Douglas J. Browne, Groton, MA (US)

(73) Assignee: Rapid Micro Biosystems, Inc., Lowell, MA (US)

( * ) Notice: Subject to any disclaimer, the term of this patent is extended or adjusted under 35 U.S.C. 154(b) by 366 days.

(21) Appl. No.: 14/355,152

(22) PCT Filed: Nov. 7, 2012

(86) PCT No.: PCT/US2012/063904
§ 371 (c)(1),
(2) Date: Apr. 29, 2014

(87) PCT Pub. No.: WO2013/070730
PCT Pub. Date: May 16, 2013

(65) Prior Publication Data
US 2014/0342447 A1    Nov. 20, 2014

Related U.S. Application Data

(60) Provisional application No. 61/624,499, filed on Apr. 16, 2012, provisional application No. 61/556,390, filed on Nov. 7, 2011.

(51) Int. Cl.
*C12M 3/00* (2006.01)
*C12Q 1/22* (2006.01)
(Continued)

(52) U.S. Cl.
CPC ............ *C12M 23/42* (2013.01); *C12M 23/00* (2013.01); *C12M 23/10* (2013.01); *C12M 23/22* (2013.01);
(Continued)

(58) Field of Classification Search
CPC ......... C12Q 1/22; C12M 23/42; C12M 23/00; C12M 23/10; C12M 23/22; C12M 41/36;
(Continued)

(56) References Cited

U.S. PATENT DOCUMENTS

| 2,672,431 A | 3/1954 | Goetz |
| 2,761,813 A | 9/1956 | Goetz |

(Continued)

FOREIGN PATENT DOCUMENTS

| AU | 760425 B2 | 3/2000 |
| CN | 2486557 Y | 4/2002 |

(Continued)

OTHER PUBLICATIONS

Extended European Search Report for European Application No. 12848583.6, mailed Jul. 15, 2015 (5 pages).

(Continued)

*Primary Examiner* — William H Beisner
*Assistant Examiner* — Danielle Henkel
(74) *Attorney, Agent, or Firm* — Clark & Elbing LLP

(57) ABSTRACT

The invention provides a device for growing cells—referred to as a cassette. The cell culturing device includes a housing that contains a lid having an optically clear window; a fluid distribution channel; a sample injection port fluidically connected to the fluid distribution channel; a base housing a porous media pad; and a media injection port fluidically connected to the media pad. The lid mates to the base to form a sterile seal; the fluid distribution channel is disposed over the media pad, which is viewable through the optical (Continued)

window; and sample fluid introduced into the fluid distribution channel is distributed evenly to the media pad, e.g., via a plurality of channels. The invention also provides kits that include cassettes of the invention and a tube set.

30 Claims, 26 Drawing Sheets

(51) Int. Cl.
    *C12M 1/00*     (2006.01)
    *C12M 1/22*     (2006.01)
    *C12M 1/12*     (2006.01)
    *C12M 1/26*     (2006.01)
    *C12M 1/34*     (2006.01)

(52) U.S. Cl.
    CPC .......... *C12M 23/38* (2013.01); *C12M 25/02* (2013.01); *C12M 25/14* (2013.01); *C12M 29/00* (2013.01); *C12M 33/00* (2013.01); *C12M 41/36* (2013.01); *C12Q 1/22* (2013.01)

(58) Field of Classification Search
    CPC ...... C12M 25/02; C12M 25/14; C12M 29/00; C12M 33/00; C12M 23/38
    See application file for complete search history.

(56) References Cited

U.S. PATENT DOCUMENTS

| | | |
|---|---|---|
| 3,694,317 A | 9/1972 | Scher |
| 3,981,776 A | 9/1976 | Saxholm |
| 4,097,586 A | 6/1978 | Gross |
| 4,098,876 A | 7/1978 | Piasio et al. |
| 4,115,535 A | 9/1978 | Giaever |
| 4,125,375 A | 11/1978 | Hunter |
| 4,129,419 A | 12/1978 | Hermann, Jr. |
| 4,141,687 A | 2/1979 | Forrest et al. |
| 4,157,323 A | 6/1979 | Yen et al. |
| 4,177,253 A | 12/1979 | Davies et al. |
| 4,222,744 A | 9/1980 | McConnell |
| 4,436,826 A | 3/1984 | Wang |
| 4,438,068 A | 3/1984 | Forrest |
| 4,454,233 A | 6/1984 | Wang |
| 4,455,370 A | 6/1984 | Bartelsman et al. |
| 4,477,578 A | 10/1984 | Miles et al. |
| 4,537,861 A | 8/1985 | Elings et al. |
| 4,562,157 A | 12/1985 | Lowe et al. |
| 4,565,783 A | 1/1986 | Hansen et al. |
| 4,582,810 A | 4/1986 | Rosenstein |
| 4,587,213 A | 5/1986 | Malecki |
| 4,598,050 A | 7/1986 | Brown |
| 4,614,585 A | 9/1986 | Mehra et al. |
| 4,693,972 A | 9/1987 | Mansour et al. |
| 4,731,337 A | 3/1988 | Luotola et al. |
| 4,745,077 A | 5/1988 | Holian et al. |
| 4,750,820 A | 6/1988 | Pareigat |
| 4,775,628 A | 10/1988 | Takakura et al. |
| 4,777,137 A | 10/1988 | Lemonnier |
| 4,777,145 A | 10/1988 | Luotola et al. |
| 4,912,037 A | 3/1990 | Lemonnier |
| 4,922,092 A | 5/1990 | Rushbrooke et al. |
| 4,959,301 A | 9/1990 | Weaver et al. |
| 4,981,793 A | 1/1991 | Johnson et al. |
| 4,988,302 A | 1/1991 | Smith et al. |
| 4,988,618 A | 1/1991 | Li et al. |
| 5,073,497 A | 12/1991 | Schwartz |
| 5,089,413 A | 2/1992 | Nelson et al. |
| 5,130,733 A | 7/1992 | Taniguchi et al. |
| 5,137,812 A | 8/1992 | Matner |
| 5,190,666 A | 3/1993 | Bisconte |
| 5,232,838 A | 8/1993 | Nelson et al. |
| 5,238,810 A | 8/1993 | Fujiwara et al. |
| 5,258,284 A | 11/1993 | Morris, Jr. et al. |
| 5,262,526 A | 11/1993 | Sasamoto et al. |
| 5,292,644 A | 3/1994 | Berg |
| 5,306,420 A | 4/1994 | Bisconte |
| 5,321,545 A | 6/1994 | Bisconte |
| 5,348,885 A | 9/1994 | Labarthe |
| 5,355,215 A | 10/1994 | Schroeder et al. |
| 5,366,867 A | 11/1994 | Kawakami et al. |
| 5,464,749 A | 11/1995 | Schwarzberg et al. |
| 5,474,910 A | 12/1995 | Alfano |
| 5,510,246 A | 4/1996 | Morgan |
| 5,538,857 A | 7/1996 | Rosenthal et al. |
| 5,541,069 A | 7/1996 | Mortensen et al. |
| 5,552,272 A | 9/1996 | Bogart |
| 5,558,839 A | 9/1996 | Matte et al. |
| 5,582,982 A | 12/1996 | Cubbage et al. |
| 5,585,241 A | 12/1996 | Lindmo |
| 5,604,351 A | 2/1997 | Bisconte |
| 5,606,413 A | 2/1997 | Bellus et al. |
| 5,624,850 A | 4/1997 | Kumar et al. |
| 5,653,939 A | 8/1997 | Hollis et al. |
| 5,663,057 A | 9/1997 | Drocourt et al. |
| 5,672,880 A | 9/1997 | Kain |
| 5,681,530 A | 10/1997 | Kuster et al. |
| 5,681,712 A | 10/1997 | Nelson |
| 5,694,478 A | 12/1997 | Braier et al. |
| 5,705,402 A | 1/1998 | Leland et al. |
| 5,736,405 A | 4/1998 | Alfano et al. |
| 5,744,322 A | 4/1998 | Krejcarek et al. |
| 5,766,868 A | 6/1998 | Seto |
| 5,792,617 A | 8/1998 | Rotman |
| 5,814,454 A | 9/1998 | Ju |
| 5,821,066 A | 10/1998 | Pyle et al. |
| 5,828,716 A | 10/1998 | Bisconte de Saint Julien |
| 5,843,766 A | 12/1998 | Applegate et al. |
| 5,852,498 A | 12/1998 | Youvan et al. |
| 5,861,251 A | 1/1999 | Park et al. |
| 5,861,270 A | 1/1999 | Nelis |
| 5,861,306 A | 1/1999 | Pugh et al. |
| 5,891,394 A | 4/1999 | Drocourt et al. |
| 5,914,245 A | 6/1999 | Bylina et al. |
| 5,958,790 A | 9/1999 | Cerny |
| 5,968,766 A | 10/1999 | Powers |
| 5,976,892 A | 11/1999 | Bisconte |
| 5,981,180 A | 11/1999 | Chandler et al. |
| 5,985,675 A | 11/1999 | Charm et al. |
| 5,993,740 A | 11/1999 | Niiyama et al. |
| 6,048,723 A | 4/2000 | Banes |
| 6,051,395 A | 4/2000 | Rocco |
| 6,121,055 A | 9/2000 | Hargreaves |
| 6,122,396 A | 9/2000 | King et al. |
| 6,130,931 A | 10/2000 | Laurila et al. |
| 6,140,653 A | 10/2000 | Che |
| 6,165,742 A | 12/2000 | Ofjord et al. |
| 6,171,780 B1 | 1/2001 | Pham et al. |
| 6,200,762 B1 | 3/2001 | Zlokarnik et al. |
| 6,214,560 B1 | 4/2001 | Yguerabide et al. |
| 6,258,326 B1 | 7/2001 | Modlin |
| 6,259,807 B1 | 7/2001 | Ravkin |
| 6,268,222 B1 | 7/2001 | Chandler et al. |
| 6,274,384 B1 | 8/2001 | Starzl et al. |
| 6,287,849 B1 | 9/2001 | McNerney et al. |
| 6,306,589 B1 | 10/2001 | Muller et al. |
| 6,309,822 B1 | 10/2001 | Fodor et al. |
| 6,345,115 B1 | 2/2002 | Ramm et al. |
| 6,358,730 B1 | 3/2002 | Kane |
| 6,472,166 B1 | 10/2002 | Wardlaw et al. |
| 6,582,912 B1 | 6/2003 | Rousseau et al. |
| 6,602,704 B1 | 8/2003 | Maxwell et al. |
| 6,623,983 B1 | 9/2003 | Terstappen et al. |
| 6,664,528 B1 | 12/2003 | Cartlidge et al. |
| 6,710,879 B1 | 3/2004 | Hansen et al. |
| 6,727,071 B1 | 4/2004 | Dunlay et al. |
| 6,764,648 B1 | 7/2004 | Roach et al. |
| 6,790,655 B2 | 9/2004 | Lyman et al. |
| 6,792,132 B1 | 9/2004 | Hara et al. |
| 6,852,527 B2 | 2/2005 | Chan et al. |
| 6,919,960 B2 | 7/2005 | Hansen et al. |
| 6,969,607 B2 | 11/2005 | Minton |
| 7,068,365 B2 | 6/2006 | Hansen et al. |

(56) References Cited

U.S. PATENT DOCUMENTS

| | | | |
|---|---|---|---|
| 7,160,687 B1 | 1/2007 | Kapur et al. | |
| 7,582,415 B2 | 9/2009 | Straus | |
| 7,763,405 B2 | 7/2010 | Wu et al. | |
| 7,763,455 B2 | 7/2010 | Cima et al. | |
| 7,820,430 B2 | 10/2010 | Weng et al. | |
| 9,057,046 B2 | 6/2015 | Browne et al. | |
| 2001/0039060 A1 | 11/2001 | Siiman et al. | |
| 2002/0028471 A1 | 3/2002 | Oberhardt | |
| 2002/0055092 A1 | 5/2002 | Hochman | |
| 2002/0137106 A1 | 9/2002 | Leung et al. | |
| 2004/0048395 A1 | 3/2004 | Lee et al. | |
| 2004/0171121 A1 | 9/2004 | Leppla et al. | |
| 2004/0172000 A1 | 9/2004 | Roe et al. | |
| 2004/0246483 A1 | 12/2004 | Hansen et al. | |
| 2005/0013737 A1 | 1/2005 | Chow et al. | |
| 2005/0148085 A1 | 7/2005 | Larsen | |
| 2005/0153430 A1 | 7/2005 | Ohtaka | |
| 2005/0191687 A1 | 9/2005 | Wang et al. | |
| 2005/0220670 A1 | 10/2005 | Palmieri et al. | |
| 2005/0221403 A1 | 10/2005 | Gazenko | |
| 2005/0225766 A1 | 10/2005 | Hansen et al. | |
| 2005/0226779 A1 | 10/2005 | Oldham et al. | |
| 2006/0006067 A1 | 1/2006 | Unger | |
| 2006/0051816 A1 | 3/2006 | Hsieh et al. | |
| 2006/0121055 A1 | 6/2006 | Campbell et al. | |
| 2006/0129327 A1 | 6/2006 | Kim et al. | |
| 2006/0188967 A1 | 8/2006 | Nalin et al. | |
| 2006/0210435 A1 | 9/2006 | Alavie et al. | |
| 2006/0216696 A1 | 9/2006 | Goguen | |
| 2006/0256340 A1 | 11/2006 | Hansen et al. | |
| 2006/0292552 A1 | 12/2006 | Haquette et al. | |
| 2007/0014695 A1 | 1/2007 | Yue et al. | |
| 2007/0105185 A1 | 5/2007 | Cima et al. | |
| 2007/0184546 A1 | 8/2007 | Farrelly et al. | |
| 2007/0212681 A1 | 9/2007 | Shapiro et al. | |
| 2007/0212747 A1* | 9/2007 | Browne | C12M 25/02 435/34 |
| 2008/0003571 A1 | 1/2008 | McKernan et al. | |
| 2008/0014576 A1 | 1/2008 | Jovanovich et al. | |
| 2008/0032328 A1 | 2/2008 | Cline et al. | |
| 2008/0038738 A1 | 2/2008 | Weigum et al. | |
| 2008/0200343 A1 | 8/2008 | Clemens et al. | |
| 2008/0206099 A1 | 8/2008 | Aruga et al. | |
| 2009/0311776 A1* | 12/2009 | Kelly, Jr. | C12M 23/20 435/289.1 |
| 2013/0011566 A1 | 1/2013 | Colin et al. | |
| 2015/0072377 A1 | 3/2015 | Browne et al. | |

FOREIGN PATENT DOCUMENTS

| | | |
|---|---|---|
| DE | 19608320 A1 | 8/1997 |
| DE | 19631997 A1 | 2/1998 |
| DE | 19940810 A1 | 5/2000 |
| EP | 0171174 A2 | 2/1986 |
| EP | 0574977 A1 | 12/1993 |
| EP | 1207394 A2 | 5/2002 |
| EP | 1508374 A2 | 2/2005 |
| EP | 1985693 A1 | 10/2008 |
| JP | H3-83598 A | 4/1991 |
| JP | H03102240 A | 4/1991 |
| JP | H10295362 A | 11/1998 |
| JP | H11346795 A | 12/1999 |
| JP | 2000509827 A | 8/2000 |
| JP | 2001224355 A | 8/2001 |
| JP | 2001512875 A | 8/2001 |
| JP | 2002125656 A | 5/2002 |
| JP | 2003294596 A | 10/2003 |
| JP | 2006087336 A | 4/2006 |
| JP | 2006-162466 A | 6/2006 |
| JP | 2008-96223 A | 4/2008 |
| WO | WO-83/01581 A1 | 5/1983 |
| WO | WO-86/04684 A1 | 8/1986 |
| WO | WO-89/05456 A1 | 6/1989 |
| WO | WO-92/05448 A2 | 4/1992 |
| WO | WO-93/24608 A1 | 12/1993 |
| WO | WO-97/40181 A1 | 10/1997 |
| WO | WO-97/44664 A1 | 11/1997 |
| WO | WO-98/31783 A1 | 7/1998 |
| WO | WO-98/38490 A1 | 9/1998 |
| WO | WO-98/50577 A1 | 11/1998 |
| WO | WO-99/08233 A1 | 2/1999 |
| WO | WO-99/20789 A1 | 4/1999 |
| WO | WO-99/36577 A1 | 7/1999 |
| WO | WO-99/40176 A1 | 8/1999 |
| WO | WO-99/58948 A2 | 11/1999 |
| WO | WO-00/04382 A1 | 1/2000 |
| WO | WO-00/47766 A1 | 8/2000 |
| WO | WO-01/57522 A2 | 8/2001 |
| WO | WO-01/61348 A1 | 8/2001 |
| WO | WO-2005/082254 A2 | 9/2005 |
| WO | WO-2006/032044 A2 | 3/2006 |
| WO | WO-2008/005998 A2 | 1/2008 |

OTHER PUBLICATIONS

Synbiosis, "What's New: Innovative Plate Holder for ProtoCOL," <http://www.synbiosis.com/synbiosis/moreinfo.asp?p.=BR29>, retrieved Oct. 16, 2002 (2 pages).

Perceptive Instruments Ltd., "Sorcerer Automated Colony Counting," <www.perceptive.co.uk>, (2 pages) (2002).

Perceptive Instruments Ltd., "Technical Specification," <http://www.perceptive.co.uk/products/scc/techspec.htm>, retrieved Apr. 12, 2005 (2 pages).

Al-Hakiem et al., "Development of fluoroimmunoassays for the determination of individual or combined levels of procainamide and n-acetylprocainamide in serum." J Immunoassay. 3(1):91-110 (1982).

Allman et al., "Fluoroimmunoassay of progesterone in human serum or plasma," Clin Chem. 27(7):1176-9 (1981).

BioLogics, "Colony Counter Models and Specifications," <http://biologics-inc.com/cc-models.htm>, retrieved Apr. 15, 2005 (3 pages).

Catalogue of Becton, Dickinson and Company, p. 28, 29, 32-35, 150 and 151, Japan, (2003).

Clean Technology, 5(8), 60-61 (1995) (No English translation provided).

Corkidi et al., "COVASIAM: an image analysis method that allows detection of confluent microbial colonies and colonies of various sizes for automated counting," Appl Environ Microbiol. 64(4):1400-4 (1998).

Loats Associates, Inc., "Digital Multi-Purpose High-Resolution Colony and Plaque Counter",<http://www.loats.com/mla.html>, retrieved Apr. 12, 2005 (3 pages).

Esteban et al., "Improved direct epifluorescent filter technique for rapid bioburden control in intravenous solutions." J Parenter Sci Technol. 46(5):146-9 (1992).

Findlay et al., "Automated closed-vessel system for in vitro diagnostics based on polymerase chain reaction," Clin Chem. 39(9):1927-33 (1993).

Freydiere et al., "Detection of salmonellae by using Rambach agar and by a C8 esterase spot test," J Clin Microbiol. 29(10):2357-9 (1991).

Frost, "Improved technic for the micro or little plate method of counting bacteria in milk," J Infect Dis. 28(2):176-184 (1921).

Gray et al., "Identification of micro-organisms after milliflex rapid detection—a possibility to identify nonsterile findings in the milliflex rapid sterility test," PDA J Pharm Sci Technol. 65(1):42-54 (2011).

International Preliminary Report on Patentability for International Application No. PCT/US2012/063904, dated Jul. 15, 2014 (6 pages).

International Search Report and Written Opinion for International Application No. PCT/US12/63904, dated Feb. 1, 2013 (18 pages).

Kamentsky, "Laser scanning cytometry," Methods Cell Biol. 63: 51-87 (2001).

Kepner et al., "Use of fluorochromes for direct enumeration of total bacteria in environmental samples: past and present," Microbiol Rev. 58(4):603-15 (1994).

(56) References Cited

OTHER PUBLICATIONS

Kroll et al., "A laser-light pulse counting method for automatic and sensitive counting of bacteria stained with acridine orange," J Appl Bacteriol. 66(2):161-7 (1989).

Lamture et al., "Direct detection of nucleic acid hybridization on the surface of a charge coupled device," Nucleic Acids Res. 22(11): 2121-5 (1994).

Loats Associates Inc. System Specifications, "Ordering from Loats Associates, Inc.," <http://www.loats.com/order_info.html>, retrieved Apr. 12, 2005 (7 pages).

Loats et al., "LAI High-Resolution Automated Colony Counting System—Mouse Lymphoma Assay: Performance Analysis,"<http://loats.com/docs/HRCCval/HRCCval.htm>, retrieved on Jul. 6, 2004 (11 pages).

Logtenberg et al., "Enumeration of (auto)antibody producing cells in human using the "spot-ELISA"," Immunol Lett. 9(6): 343-347 (1985).

London et al., "An automated system for rapid non-destructive enumeration of growing microbes," PLoS One. 5(1):e8609 (16 pages) (2010).

Masuko et al., "A novel method for detection and counting of single bacteria in a wide field using an ultra-high-sensitivity tv camera without a microscope," FEMS Microbiol Lett. 65(3): 287-290 (1991).

Masuko et al., "Rapid detection and counting of single bacteria in a wide field using a photon-counting tv camera," FEMS Microbiol Lett. 67(2): 231-238 (1991).

Mignon-Godefroy et al., "Solid phase cytometry for detection of rare events," Cytometry. 27(4): 336-44 (1997).

Miraglia et al., "Homogeneous cell-and bead-based assays for high throughput screening using fluorometric microvolume assay technology," J Biomol Screen. 4(4): 193-204 (1999).

Moore et al, "Lymphocyte fractionation using immunomagnetic colloid and a dipole magnet flow cell sorter," J Biochem Biophys Methods. 37(1-2): 11-33 (1998).

Nargessi et al., "Immunoassays for serum c-reactive protein employing fluorophore-labelled reactants," J Immunol Methods. 71(1): 17-24 (1984).

Nargessi et al., "Magnetizable solid-phase fluoroimmunoassay of thyroxine by a sequential addition technique," Clin Chem. 26(12): 1701-3 (1980).

Nebe-von-Caron et al., "Analysis of bacterial function by multicolour fluorescence flow cytometry and single cell sorting," J Microbiol Methods. 42(1):97-114 (2000).

Nelis et al.,"Enzymatic detection of coliforms and *Escherichia coli* within 4 hours," Water Air Soil Pollut. 123:43-52 (2000).

Patterson, "A wide angle camera for photographic search of the ocean bottom," SPIE. C-XII-1-8 (1966).

PerkinElmer, Inc., GeneScreenTM Hybridization Transfer Membranes: transfer and detection protocols, Application Notes, available at <http://las.perkinelmer.com/>, retrieved Feb. 27, 2007 (11 pages).

Rousseau et al., "New miniaturized highly sensitive immunoassay device for quantitative measurement of soluble or particular antigen or antibodies in a liquid sample," Clin Chem. 45(9): 1685-7 (1999).

Sage et al., "A rapid and nondestructive method for microbiological testing in pharmaceutical manufacturing," American Biotechnology Laboratory. (5 pages) (2006).

Schultz et al., "Single-target molecule detection with nonbleaching multicolor optical immunolabels," Proc Natl Acad Sci U.S.A. 97(3):996-1001 (2000).

Susa et al., "Legionella pneumophila infection in intratracheally inoculated T cell-depleted or -nondepleted A/J mice," J Immunol. 160(1):316-21 (1998).

Thomas et al, "Making gold nanoparticles glow: enhanced emission from a surface-bound fluoroprobe," J Am Chem Soc. 122(11): 2655-6 (2000).

Tibbe et al., "Optical tracking and detection of immunomagnetically selected and aligned cells," Nat Biotechnol. 17(12):1210-3 (1999).

Topac, "Colony Counter," <http://www.topac.com/acolyte.html>, retrieved Apr. 12, 2005 (3 pages).

Van Poucke et al. "Solid phase cytometry-based enzymatic detection of coliforms in drinking water within 4 h", Water Supply. 17(2):67-72 (1999).

Van Poucke et al. "Rapid detection of fluorescent and chemiluminescent total coliforms and *Escherichia coli* on membrane filters," J Microbiol Methods. 42(3):233-244 (2000).

Van Poucke et al., "A 210-min solid phase cytometry test for the enumeration of *Escherichia coli* in drinking water," J Appl Microbiol. 89(3):390-6 (2000).

Vidon et al., "A simple chemiluminescence-based method for rapid enumeration of Listeria spp. microcolonies," J Appl Microbiol. 90(6):988-93 (2001).

Viinikka et al., "A two-site immunofluorometric assay for human placental lactogen," Clin Chim Acta. 114(1):1-9 (1981).

Waggoner, "Fluorescent Probes for Cytometry," Flow Cytometry and Sorting, Wiley-Liss, 209-225 (1990).

Wellman et al., "Magnetically-assisted transport evanescent field fluoroimmunoassay," Anal Chem. 78(13): 4450-6 (2006).

Wilson, "Use of the IUL Countermat Automatic Colony Counter for Spiral Plated Total Viable Counts," Appl Environ Microbiol. 61(8):3158-3160 (1995).

Wolniak, "BSCI 427 Principles of Microscopy Fall 2004 Syllabus," <http://www.life.umd.edu/cbmg/faculty/wolniak /wolniakmicro. html>, retrieved Nov. 8, 2007 (8 pages).

Yasui et al., "Imaging of Lactobacillus brevis single cells and microcolonies without a microscope by an ultrasensitive chemiluminescent enzyme immunoassay with a photon-counting television camera," Appl Environ Microbiol. 63(11): 4528-33 (1997).

Zhao et al., "Competitive immunoassay for microliter protein samples with magnetic beads and near-infrared fluorescence detection," Anal Chem. 76(7): 1871-6 (2004).

\* cited by examiner

Aerobic Cassette

Anaerobic Cassette

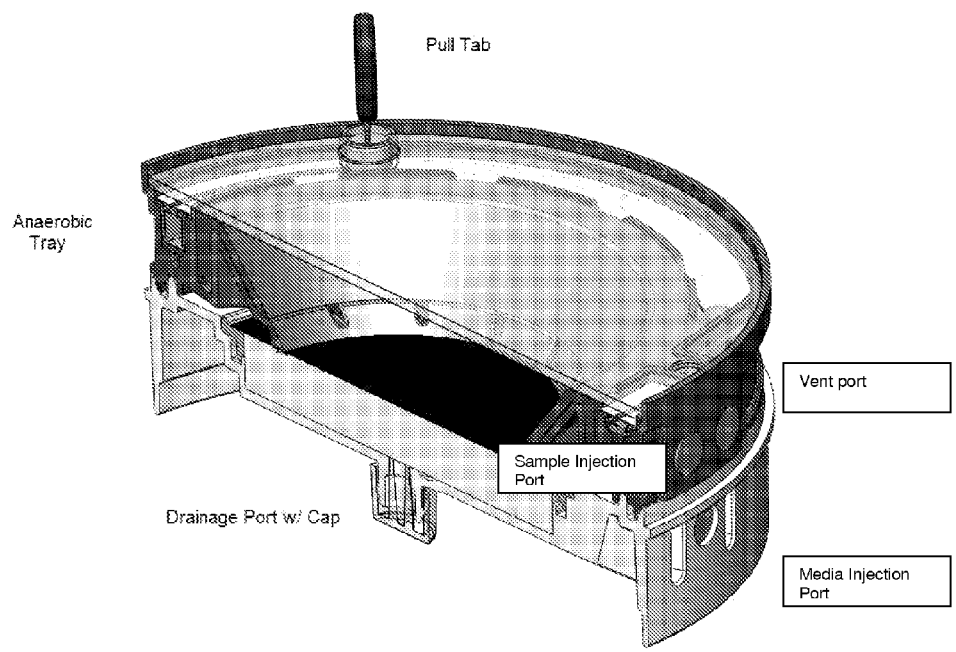
Figure 3C
Figure 3D
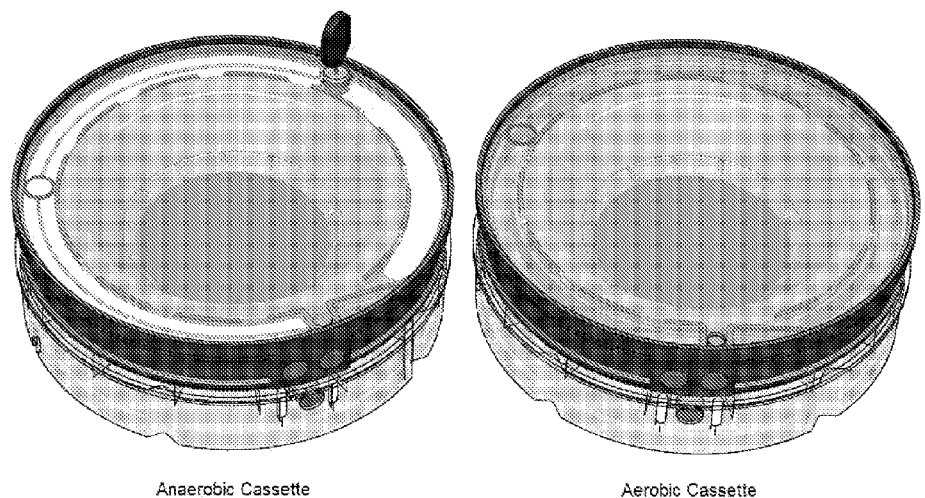

(Outer Raceway)

(Inner Raceway)

Multi Channel Fluid Path

CASSETTE FOR STERILITY TESTING

CROSS REFERENCE TO RELATED APPLICATIONS

This application claims priority under 35 U.S.C. 371 from International Application No. PCT/US2012/063904, filed Nov. 7, 2012, which claims benefit to U.S. Provisional Application Nos. 61/556,390, filed Nov. 7, 2011, and 61/624,499, filed Apr. 16, 2012, each of which is hereby incorporated by reference.

STATEMENT REGARDING FEDERALLY SPONSORED RESEARCH

This invention was made with Government support under HHSO100201000056C awarded by the Department of Health and Human Services. The Government has certain rights in the invention.

BACKGROUND OF THE INVENTION

The invention relates to the fields of cell growth and detection.

In many industries, particularly the food, beverage, healthcare, electronic, and pharmaceutical industries, it is essential to rapidly analyze samples for the degree of contamination by microorganisms, such as bacteria, yeasts, or molds.

One microbial culture technique, called microbial enumeration or colony counting, quantifies the number of microbial cells in a sample. The microbial enumeration method, which is based on in situ microbial replication, generally yields one visually detectable "colony" for each culturable microbial cell or clump of cells in the sample, referred to as a colony forming unit or CFU. Thus, counting the visible colonies allows microbiologists to determine the number of microbial CFUs in a sample accurately. To perform microbial enumeration, bacterial cells can be dispersed on the surface of nutrient agar in Petri dishes ("agar plates") and incubated under conditions that permit in situ bacterial replication. Microbial enumeration is simple, ultrasensitive, inexpensive, and quantitative but is also typically slow. The long time required results in increased costs in healthcare and in manufacturing.

There is a need for additional culturing devices and methods for microbial enumeration.

SUMMARY OF THE INVENTION

The invention provides a device for growing cells—referred to as a cassette. In one aspect, the invention features a cell culturing device including a housing that contains a lid having an optically clear window (the lid may or may not be removable); a fluid distribution channel, e.g., that is a single channel or connected to a plurality of channels; a sample injection port fluidically connected to the fluid distribution channel; a base housing a porous media pad; and a media injection port fluidically connected to the media pad. The lid mates to the base to form a sterile seal; the fluid distribution channel is disposed over the media pad, which is viewable through the optical window; and sample fluid introduced into the fluid distribution channel is distributed evenly to the media pad, e.g., via a plurality of channels. In certain embodiments, the device further includes a membrane disposed on the media pad, wherein cells in the sample fluid are retained on the membrane and viewable through the optical window. Alternatively, the media pad may have a porosity sufficient to act as a membrane. The volume between the lid and membrane may be pressurizable. In other embodiments, the cassette further includes a drainage port. An oxygen scavenger sufficient to render the interior of the device anaerobic may also be included. In certain embodiments, the cassette further includes an actuator for the oxygen scavenger, e.g., that is activated by over rotation of the lid or a pull tab or push bar that is accessed through a membrane located on top of the cassette. Cassettes of the invention may include a pressure-relief valve, and/or the base may further include channels that relieve pressure in the media pad when fluid is being introduced. Cassettes may also include a media distribution channel connected to the media injection port and optionally having a plurality of outlets around the perimeter of the media pad, wherein media introduced via the media injection port is distributed evenly to the media pad via the media distribution channel. The media distribution channel may be formed, in whole or in part, by an insert in the base, e.g., a fluid ring as depicted in the figures. Cassettes may also include an oxygen indicator. In certain embodiments, the fluid distribution channel includes a helical raceway, e.g., connected to a plurality of channels. When the fluid distribution channel is a single channel, it may include a sloped circumferential region around the media pad. A cassette may also include a cover disposed on top of the fluid distribution channel. The cover may shape the fluid stream to achieve uniform distribution to the media pad through a single channel. A cassette may also further include a vent port for venting the interior of the cassette as liquids are introduced. The vent port may be self sealing, e.g., until connected to a tube set of the invention.

In a related aspect, the invention features a kit for detecting cells, comprising a cassette of the invention and a tube set including a tube having a connector that has a needle and that mates to the sample injection port, media injection port, vent port, or drainage port. The connector may further include a septum through which the needle passes, and the connector may mate to the sample injection port, media injection port, vent port, or drainage port and seal the port with the septum when the needle and tube are removed. Kits may further include second and optional third tube sets having a connector that has a needle, wherein the connectors of the tube sets mate to one of the sample injection, media injection, vent, and drainage ports. The tubes for the first, second, and optional third tube sets may share a common inlet or outlet. The connector may include a clip that snaps into the cassette. The tube set may further include a plurality of separate tubes for at least two of sample introduction, media introduction, drainage, and venting. The connector may include needles for each tube. When one of the tubes is for venting, that tube may include a filter (e.g., to prevent release of bacteria or fluids) and/or a pressure relief valve.

The cassettes and kits of the invention may be used in any method for growth, assay, or maintenance of cells, including enumeration, detection, diagnosis, or therapeutic response.

Other features and advantages will be apparent from the following description and the claims.

BRIEF DESCRIPTION OF THE DRAWINGS

FIG. 3C is a cross-section of an anaerobic cassette. FIG. 3D is a drawing of cassettes for aerobic and anaerobic use.

The figures are not necessarily to scale.

DETAILED DESCRIPTION OF THE INVENTION

The invention features devices for capturing and culturing cells (e.g., microorganisms or cells containing microorganisms) and methods of using these devices. One example is a cassette containing nutrient media that may be employed in an automated rapid enumeration system such as the Growth Direct™ system (Rapid Micro Biosystems, Inc., Bedford, Mass.), e.g., as described in U.S. Publication No. 2003/0082516, which is hereby incorporated by reference. In one embodiment, the invention provides a fully contained, closed loop, sterility test that allows the end user to filter samples through a membrane (e.g., 0.45 µm), add nutrient media to support growth, and image the cassette, e.g., on the Growth Direct™ system, without exposing the sample or other internal components to possible outside contamination. Cassettes may be used under aerobic or anaerobic conditions. Multiple cassettes may be packaged together in a kit, e.g., at least one cassette will be configured for aerobic and one configured for anaerobic testing. The invention also provides a tube set to allow for introduction of sample, the nutrient media, and/or drainage of excess fluid. The tube set may also allow even distribution of the sample across multiple cassettes.

Cassettes

In general, a cassette of the invention will include a lid having an optically clear window; a fluid distribution channel; a sample injection port fluidically connected to the fluid distribution channel; a base that houses a porous media pad; and a media injection port fluidically connected to the media pad. The sample injection port is typically located on the side of the lid but can also be located on the top. In certain embodiments, the lid is made from an optically clear material. Alternatively, the optically clear window is housed within an optical frame.

In certain embodiments, the fluid distribution channel includes a plurality of channels. Various views of such a cassette are shown in FIGS. 1A-1F. The figures shows a lid having an optically clear window, base housing a media pad, sample injection port, media injection port, and the fluid distribution channel, including a stabilizing channel, and plurality of channels for distribution of sample to the media pad. A drainage port and a membrane, which may or may not be removable, are also shown. Typically, the lid mates to the base to form a sterile seal, which may or may not be airtight. The membrane is positioned on the media pad to be viewable through the optical window. FIG. 1F shows lids made from an optically clear material or having the optically clear window housed within an optical frame. The sample injection port is located on the top of the lid but can also be located on the side.

Figure 2A:
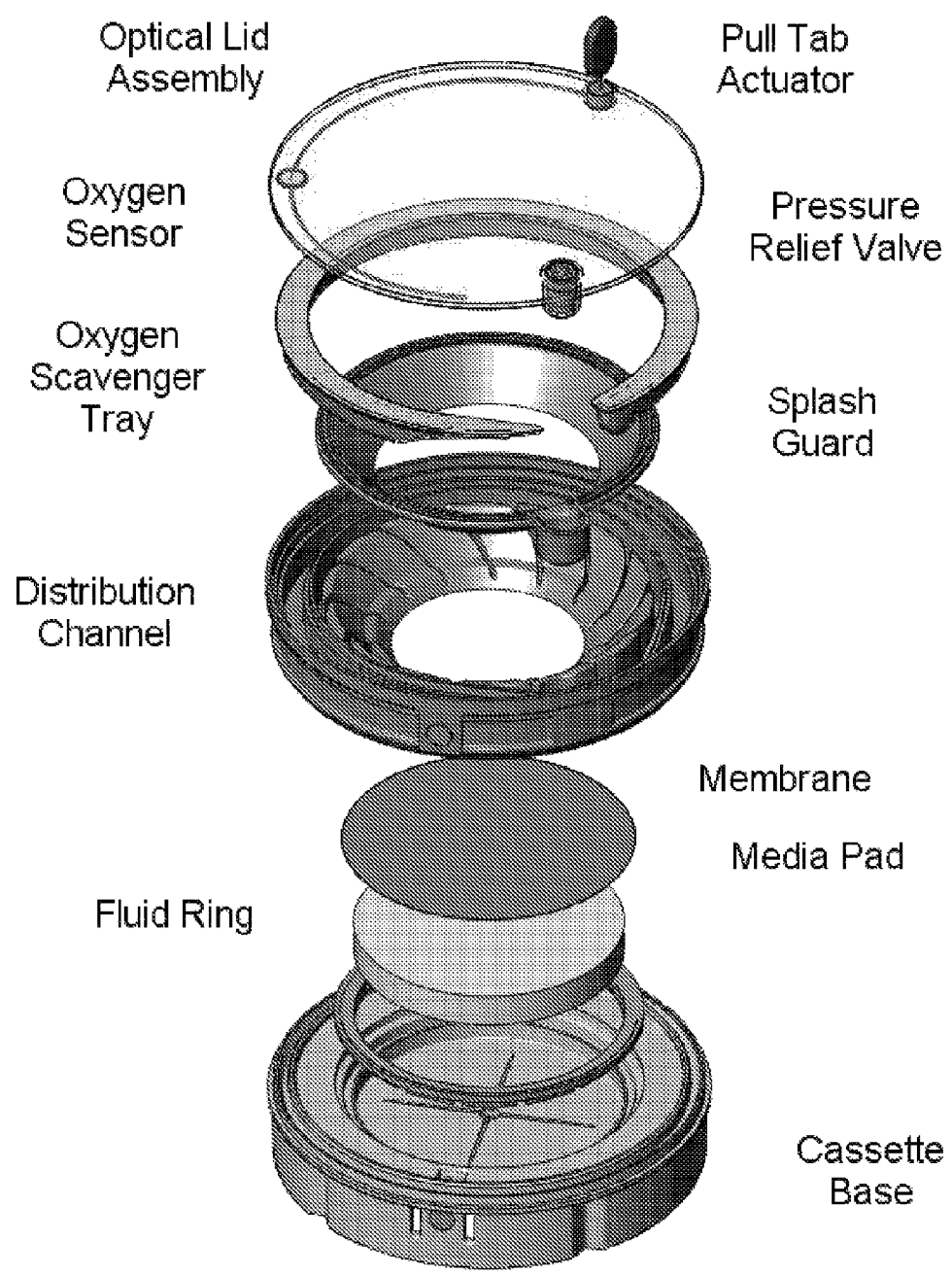
FIG. 2A is an exploded view of one embodiment of a cassette.
Figure 2B:
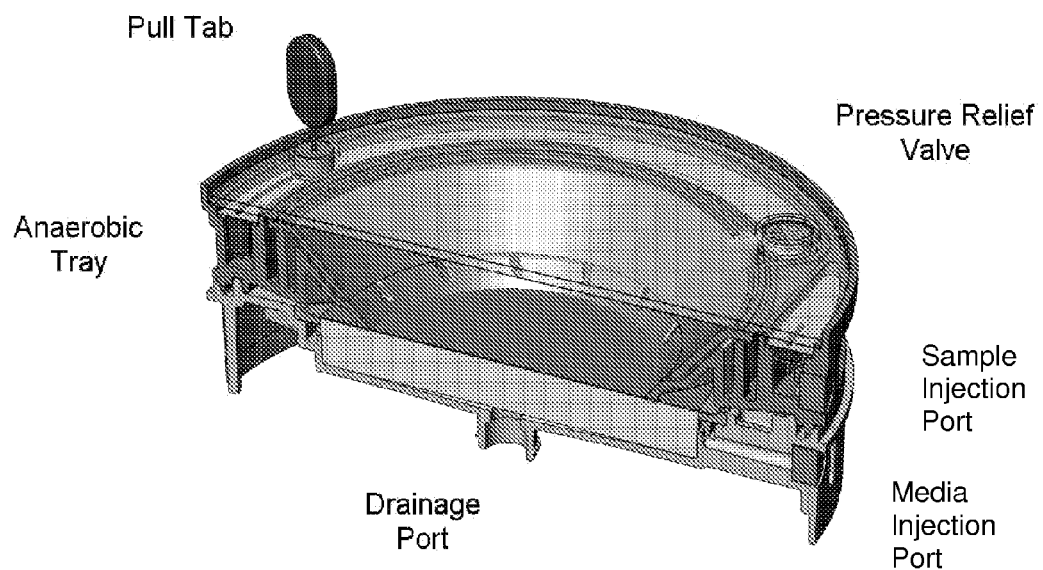
FIG. 2B is a cross-section of a cassette.
Figure 2C:
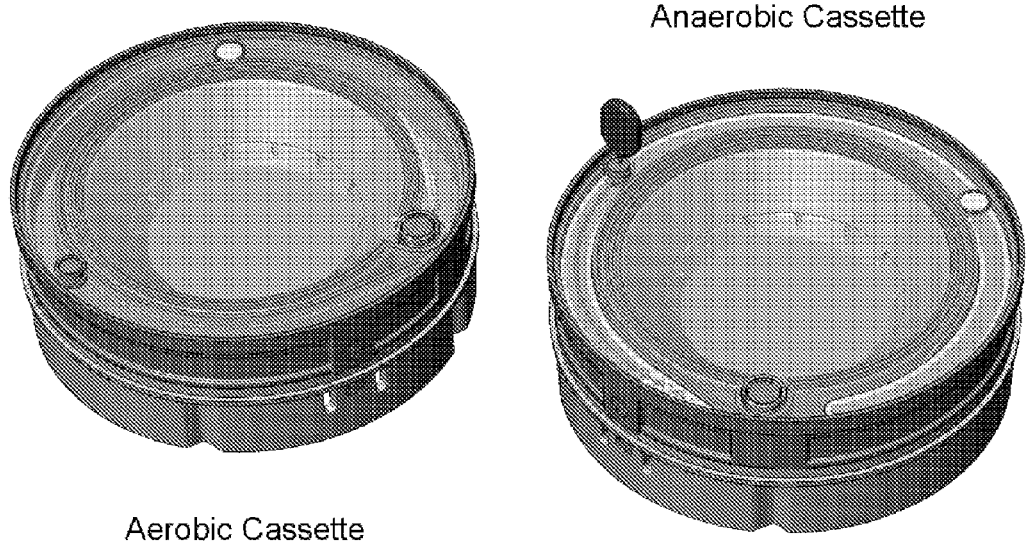
FIG. 2C is a drawing of cassettes for aerobic and anaerobic use.

Various views of an alternate cassette are shown in FIGS. 2A-2C. The figures show a lid having an optically clear window, base housing a media pad, sample injection port, media injection port, and the fluid distribution channel, including a stabilizing channel, and plurality of channels for distribution of sample to the media pad. A drainage port and a membrane, which may or may not be removable, are also shown. Typically, the lid mates to the base to form a sterile seal, which may or may not be airtight. The membrane is positioned on the media pad to be viewable through the optical window. FIG. 2C show lids having the optically clear window housed within an optical frame. Alternatively, the lid is made from an optically clear material. The sample injection port is located on the side of the lid but can also be located on the top. This cassette features a pressure relief valve in the lid.

Figure 3A:
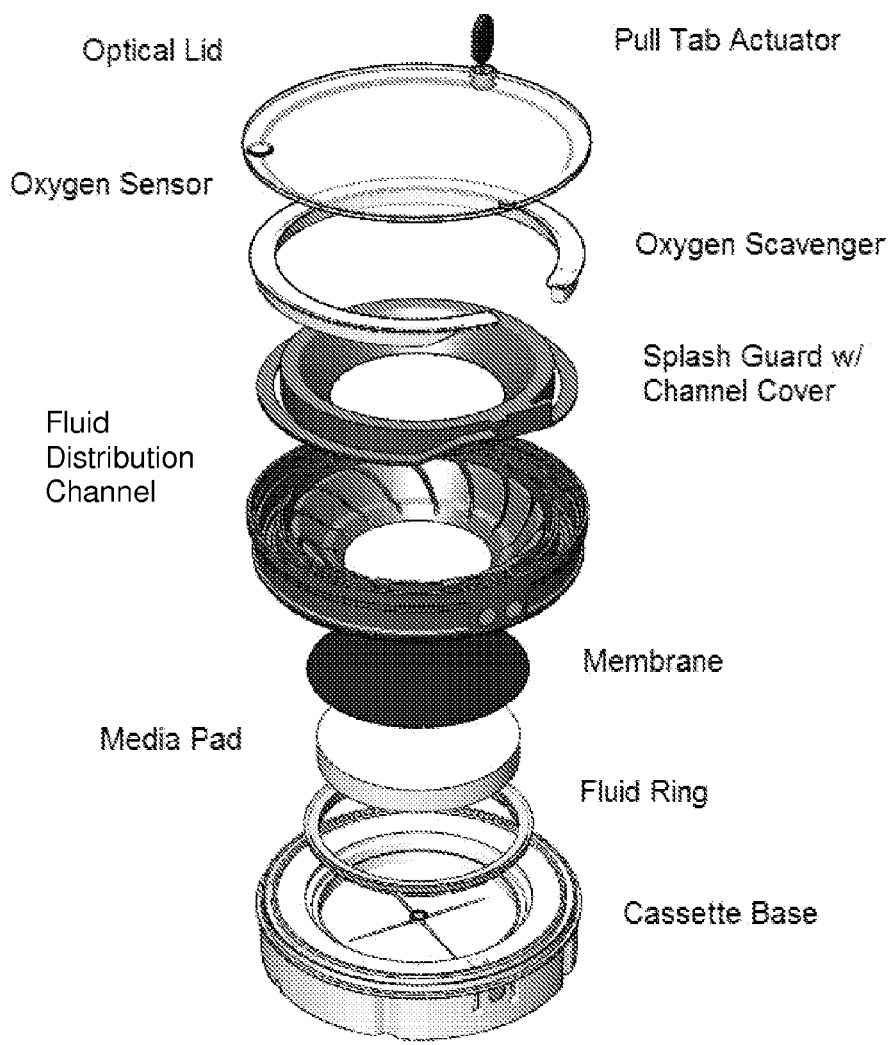
FIG. 3A is an exploded view of one embodiment of a cassette.
Figure 3B:
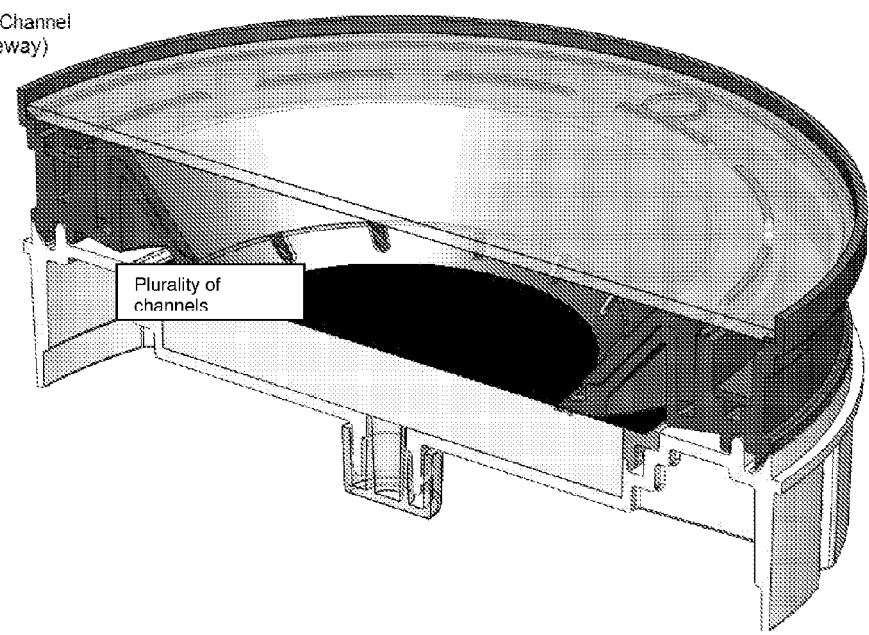
FIG. 3B is a cross-section of an aerobic cassette.

Various views of another cassette are shown in FIGS. 3A-3D. The figures show a lid having an optically clear window, base housing a media pad, sample injection port, media injection port, and the fluid distribution channel, including a stabilizing channel, and plurality of channels for distribution of sample to the media pad. A drainage port and a membrane, which may or may not be removable, are also shown. Typically, the lid mates to the base to form a sterile seal, which may or may not be airtight. The membrane is positioned on the media pad to be viewable through the optical window. FIGS. 3B and 3C show aerobic and anaerobic versions of this cassette. FIG. 3D shows lids having the optically clear window housed within an optical frame. Alternatively, the lid is made from an optically clear material. The sample injection port is located on the side of the lid but can also be located on the top. The lid also includes a venting port (FIG. 3D).

Figure 4A:
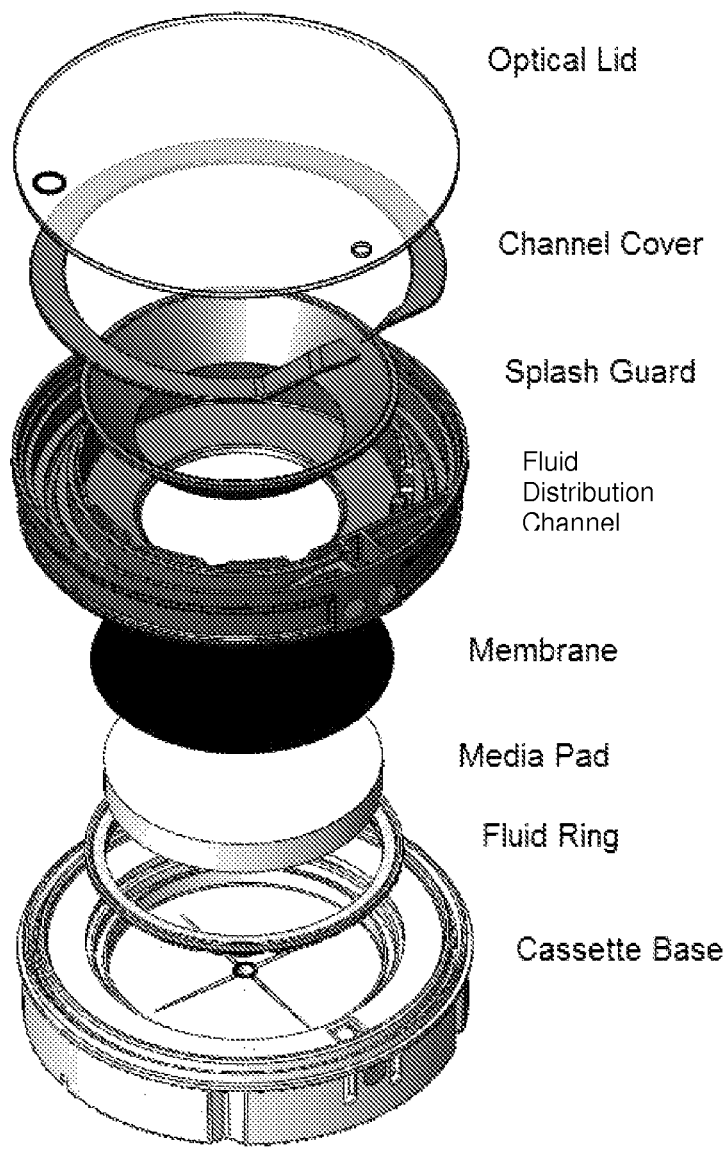
FIG. 4A is an exploded view of one embodiment of a cassette.
Figure 4B:
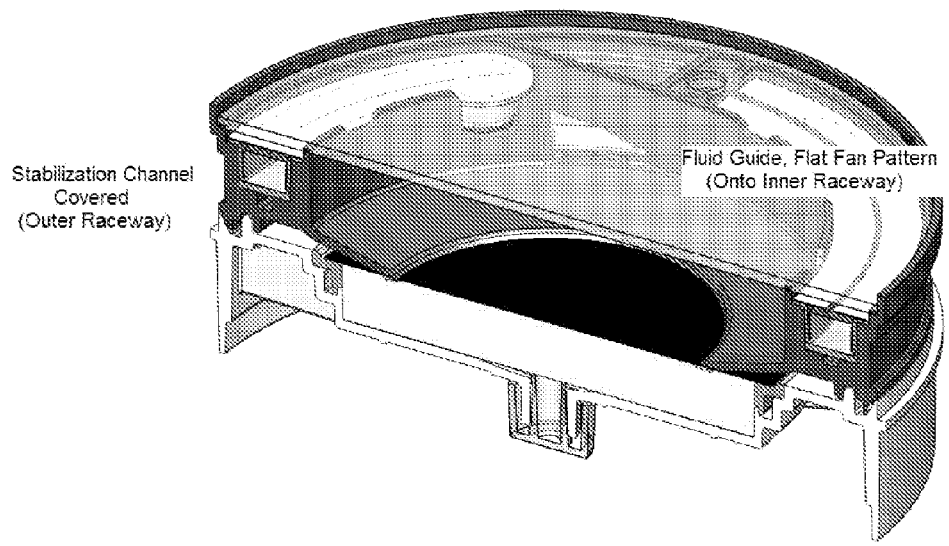
FIG. 4B is a cross-section of an anaerobic cassette.

Cassettes of the invention may include a fluid distribution channel that delivers fluid to the media pad by a single channel. Such a cassette is shown in FIGS. 4A-4B. The figures show a lid having an optically clear window, base housing a media pad, sample injection port, media injection port, and the fluid distribution channel, including a stabilizing channel for distribution of sample to the media pad. A drainage port and a membrane, which may or may not be removable, are also shown. Typically, the lid mates to the base to form a sterile seal, which may or may not be airtight. The membrane is positioned on the media pad to be viewable through the optical window. The sample injection port is located on the side of the lid but can also be located on the top. The lid also includes a venting port.

Figure 5A:
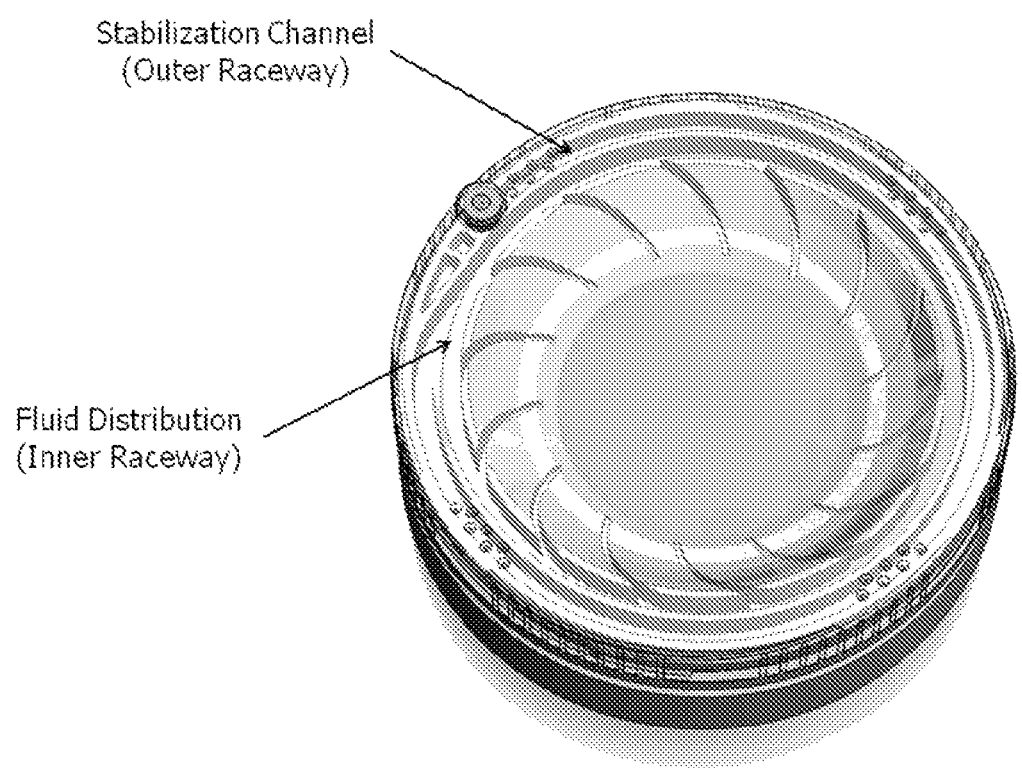
FIGS. 5A-5B are top views of cassettes including a fluid distribution channel having a helical raceway with two spirals.
Figure 5B:
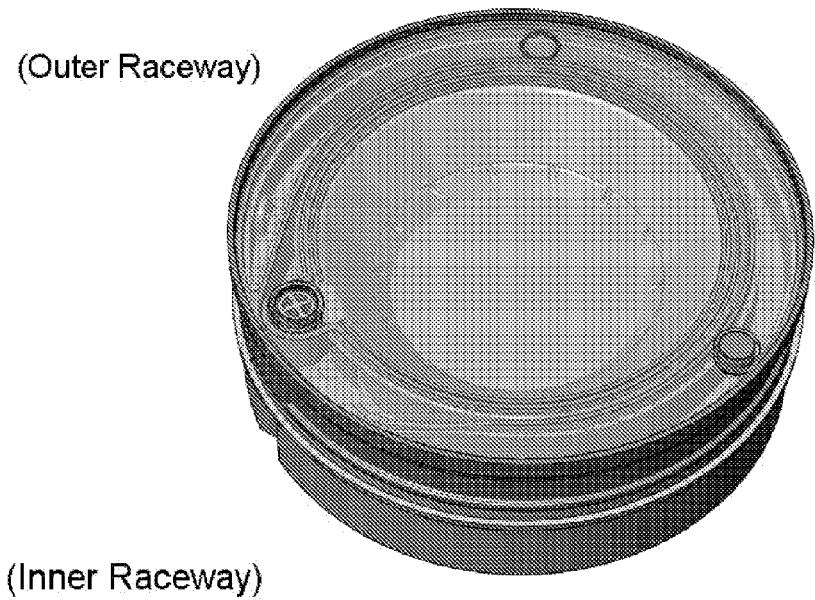
Figure 5C:
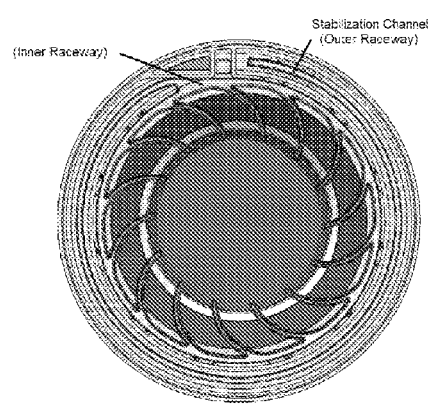
FIG. 5C is a top view of a cassette including an outer raceway and an inner raceway with a plurality of channels.
Figure 5D:
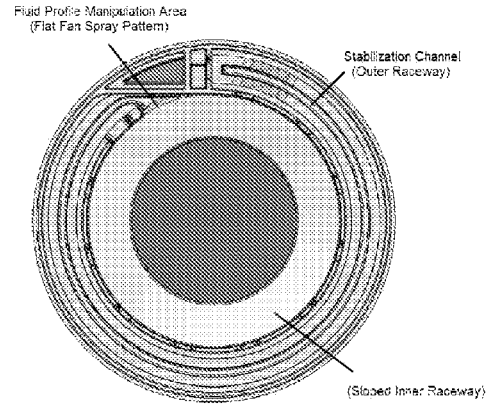
FIG. 5D is a top view of a cassette including an outer raceway and an inner raceway with a single channel.
Figure 6A:
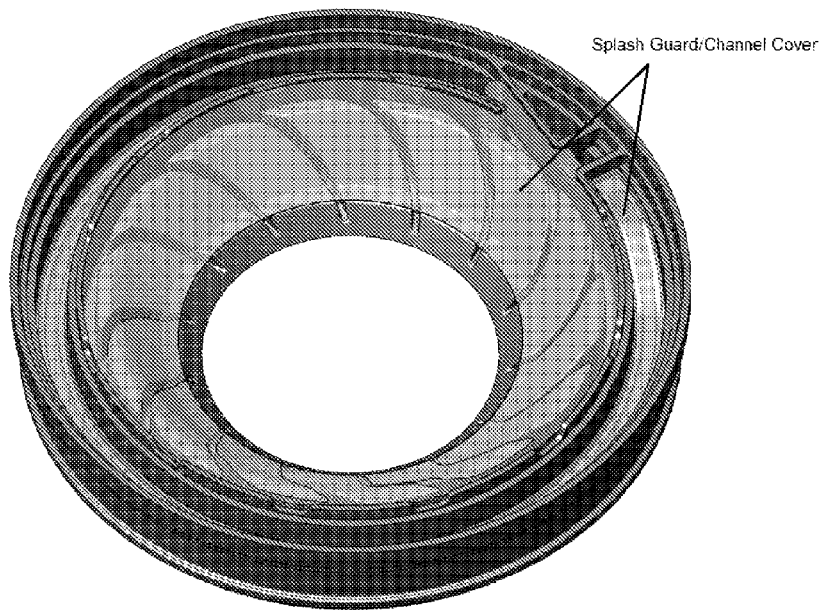
FIG. 6A is a drawing of a fluid distribution channel having a plurality of channels with a cover in place.
Figure 6B:
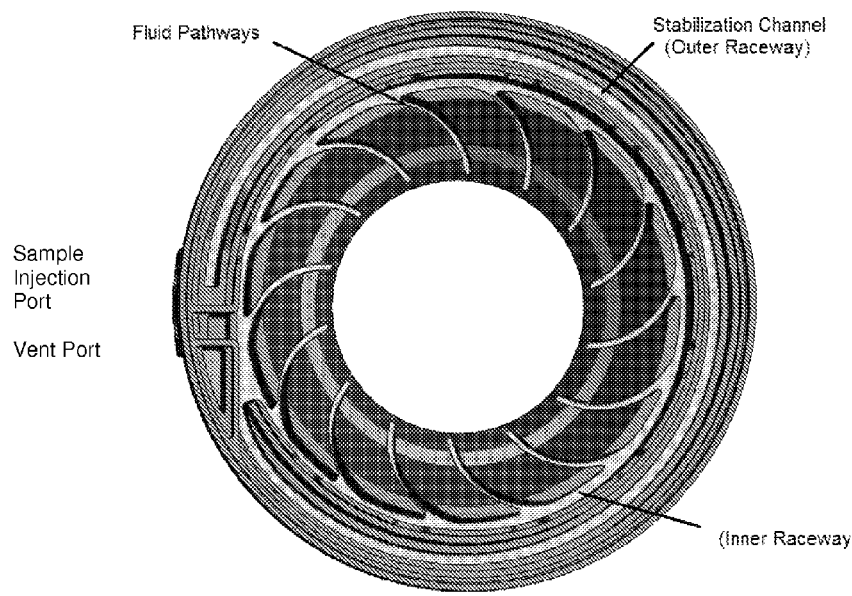
FIG. 6B is a drawing of the fluid distribution channel with the cover removed.
Figure 6C:
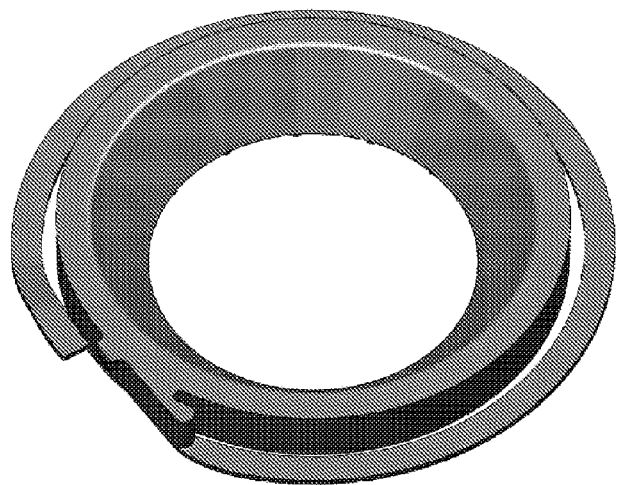
FIG. 6C is a drawing of the cover.
Figure 7A:
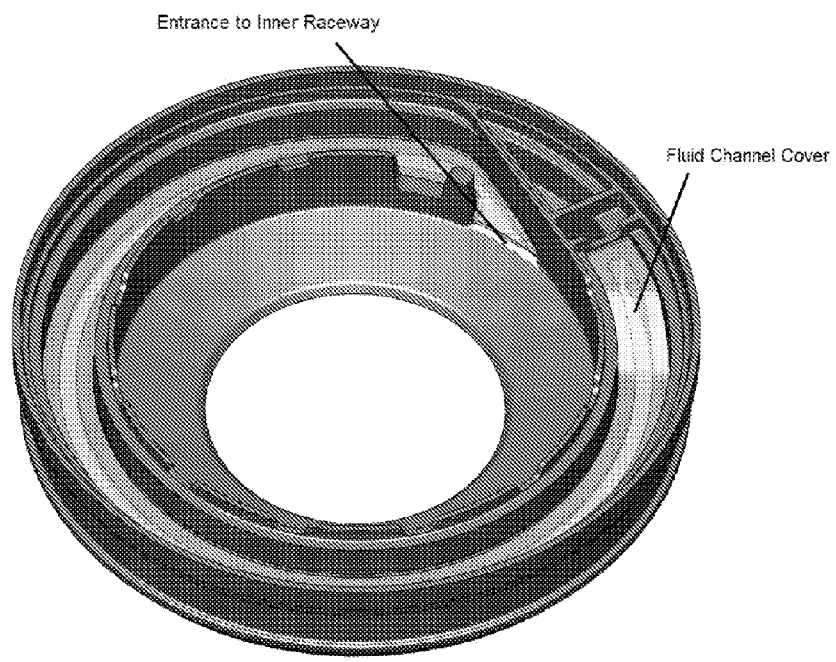
FIG. 7A is a drawing of a fluid distribution channel having a single channel with a cover in place.
Figure 7B:
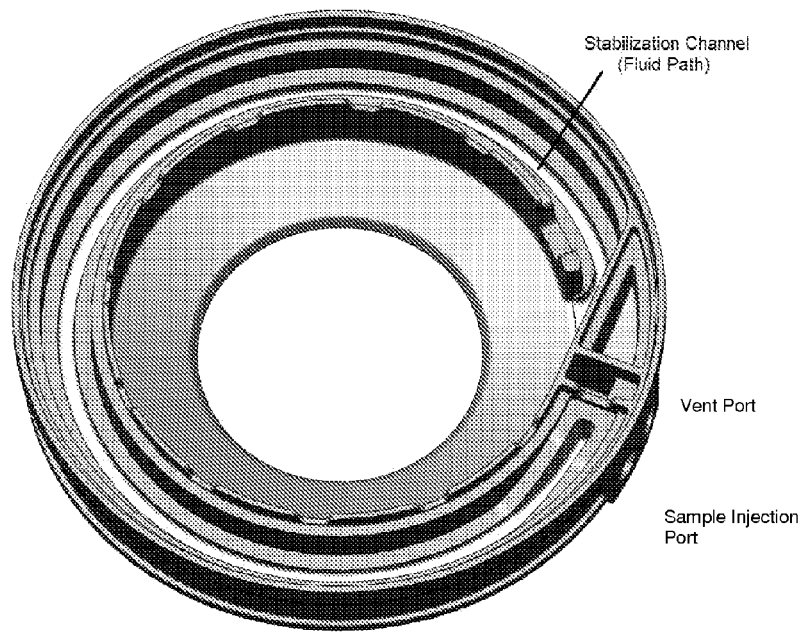
FIG. 7B is a drawing of the fluid distribution channel with the cover removed.
Figure 7C:
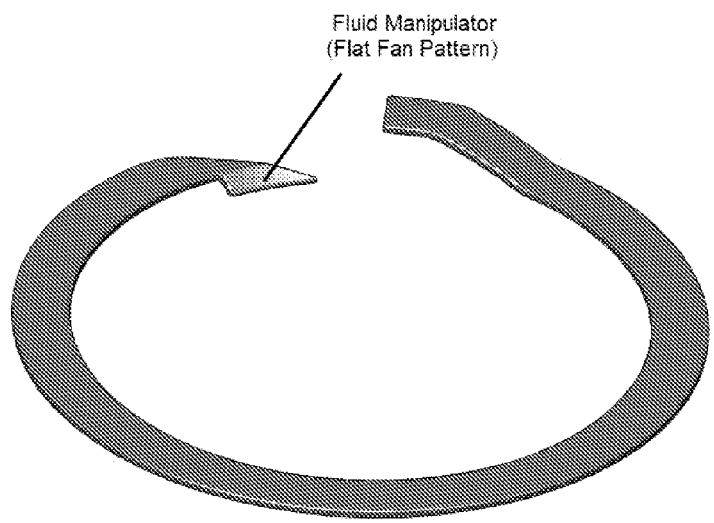
FIG. 7C is a drawing of the cover.

The fluid distribution channel may or may not include a helical raceway. The helical raceway is designed to calm excess turbulence and to distribute sample evenly to the media pad or a membrane positioned on top of the media pad, e.g., via the plurality of channels. As shown in FIGS. 5A-5C, the raceway typically includes two circuits around the device, although three or more may be employed. When present a raceway may provide fluid to the media pad via a single channel or plurality of channels (FIGS. 5A-5D). FIG. 5D shows an alternate cassette which employs a single fluid distribution channel. As shown in FIG. 5D, the cassette includes a sloped surface that circumferentially surrounds the media pad. Fluid flows around the sloped surface and onto the media pad. In cassettes with a plurality of channels leading to the media pad, the plurality of channels may also be formed on or in a sloped circumferential surface. The cassette may or may not include a component that covers the fluid distribution channel, with or without a helical raceway or plurality of channels, e.g., FIG. 1A-4B. An exemplary cover for a plurality of channels is shown in FIGS. 6A-6C. FIG. 6A shows a fluid distribution channel with a plurality of channels with the cover in place. FIG. 6B shows the fluid distribution channel with a plurality of channels. FIG. 6C shows the cover for a plurality of channels. An exemplary cover for a single fluid distribution channel is shown in FIGS. 7A-7C. FIG. 7A shows a fluid distribution channel with a single channel with the cover in place. FIG. 7B shows the single fluid distribution channel. FIG. 7C shows the cover for the single channel. This cover includes a fluid manipulator that reduces the column height of the fluid distribution channel as it enters a sloped circumferential region. The fluid manipulator may also cause the fluid to fan out along the surface leading to the media pad. Cassettes may also include a splash guard position over the fluid distribution channel where the sample is delivered to the media pad. The splash guard may form port of a cover or be a separate component. The edges of the media pad and membrane, if present, are typically covered by the fluid distribution channel or cover or splash guard to prevent the edges from being imaged.

Figure 8:
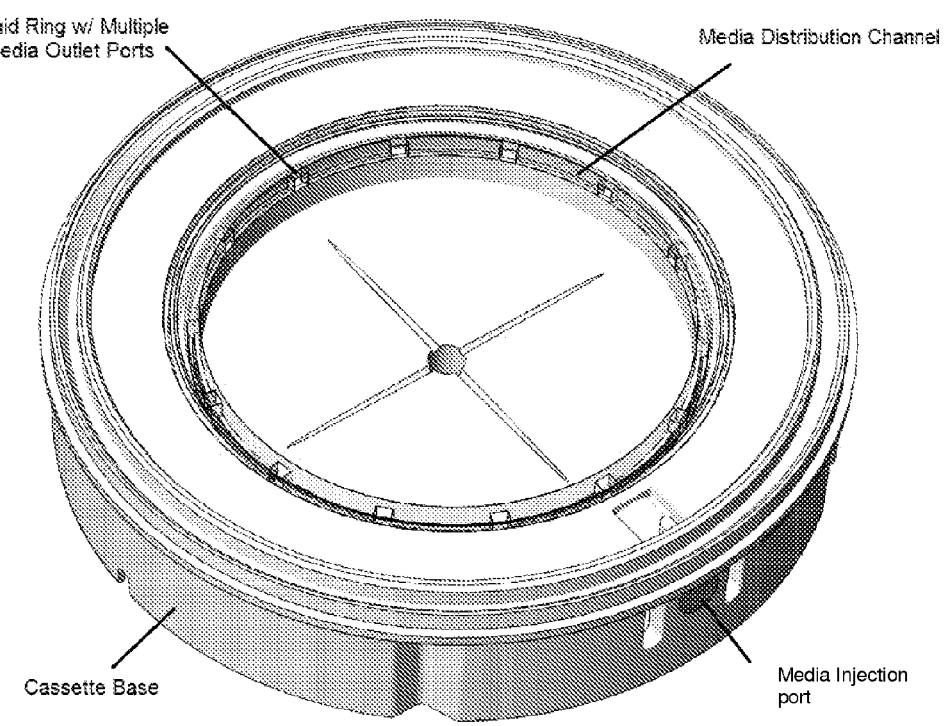
FIG. 8 is a drawing of a cassette base.

The media pad is designed to house medium for the growth or maintenance of cells. In certain embodiments, the media pad is sized to house media sufficient for cell growth for one week, two weeks, or longer. The medium is delivered to the pad via the media injection port. The media injection port is typically located on the side or bottom of the base. The cassette may also include a media distribution channel connected to the media injection port. The media distribution channel may have a plurality of outlets around the perimeter of the media pad to distribute media to the media pad evenly. An exemplary base with media pad is shown in FIG. 8.

The medium is liquid when introduced into the cassette and may remain a liquid in the pad or gel or otherwise solidify within the pad. Examples include LB broth or Sabouraud dextrose agar (SDA), R2A agar, tryptic soy agar (TSA), plate count agar (PCA), Schaedler's blood agar or similar media without the agar solidifying agent. A membrane may be placed on the media pad, e.g., between the fluid distribution channel and the pad. The membrane has pores capable of retaining cells of interest while passing fluids. Examples of pore sizes are 0.45 µm and 0.22 µm. The membrane may be separable or integral to the media pad. Alternatively, the surface of the media pad may be fabricated or treated to produce the membrane.

Figure 1A:
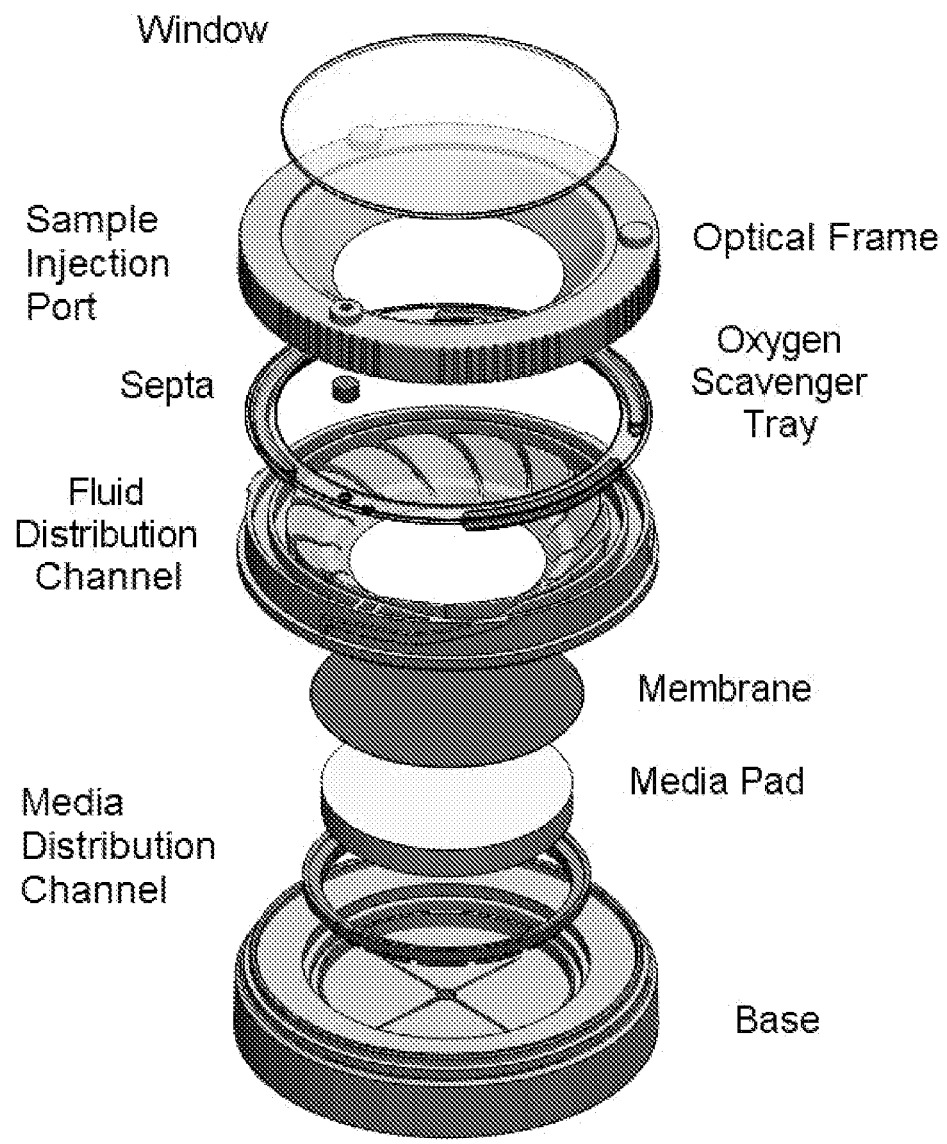
FIGS. 1A and 1C are exploded views of cassettes.
Figure 1B:
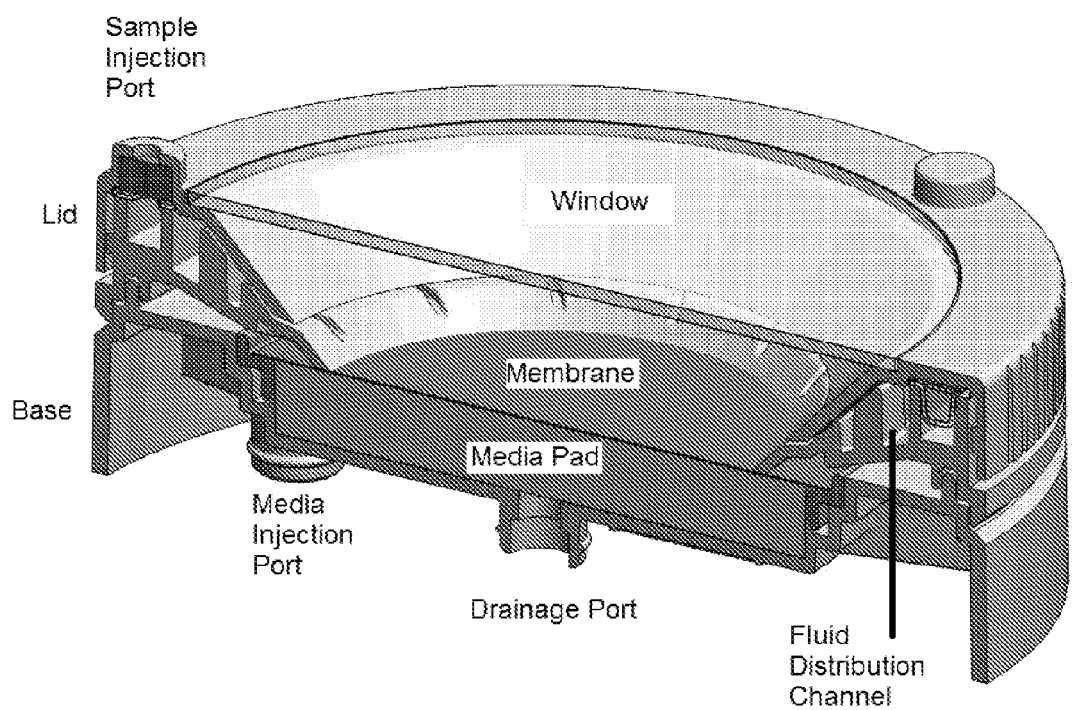
FIG. 1B is a cross-section of a cassette.
Figure 1C:
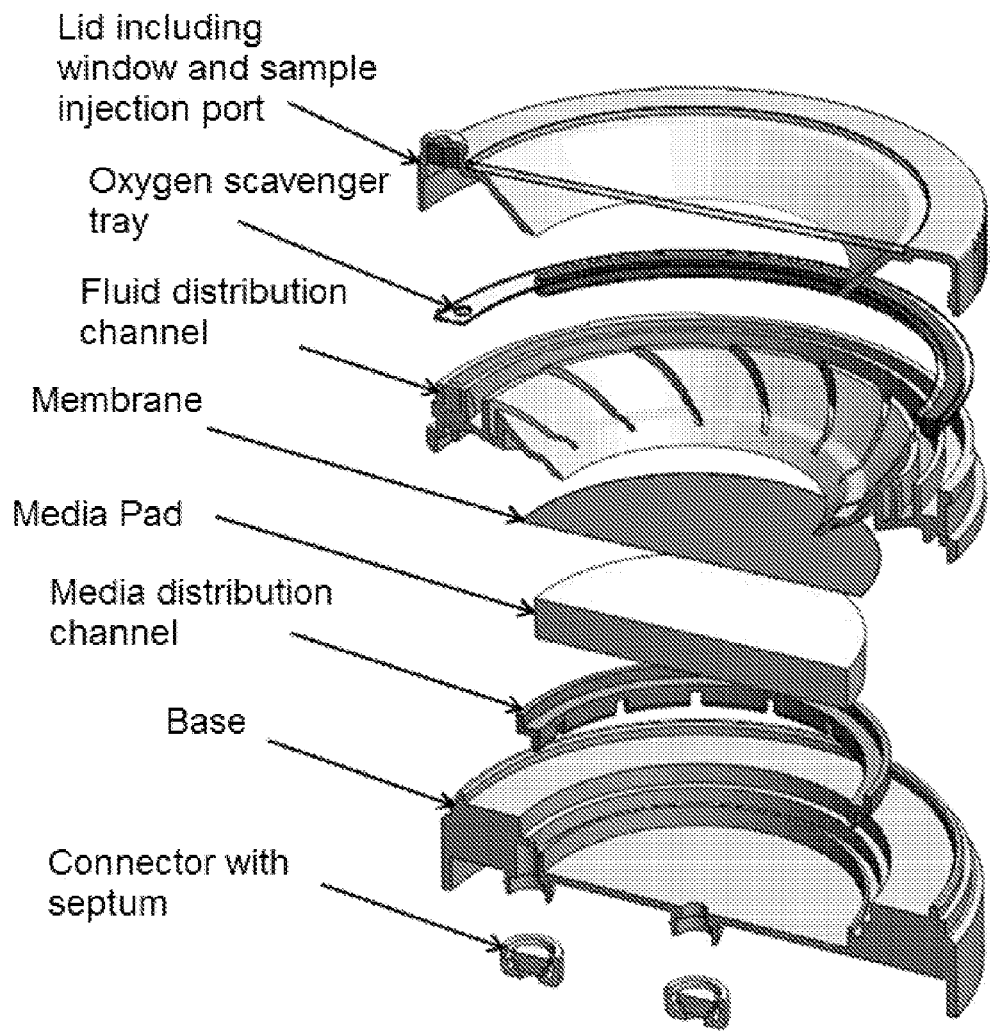
Figure 1D:
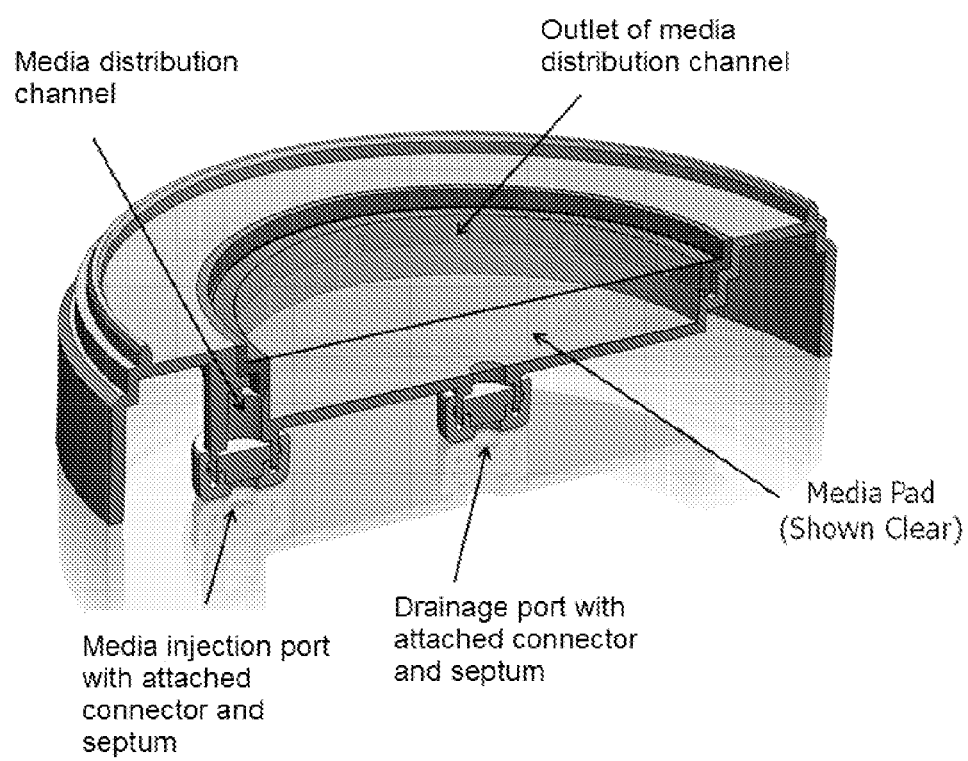
FIG. 1D is a cross-section of a base of a cassette indicating the media injection port, drainage port, media pad, and media distribution channel.
Figure 1E:
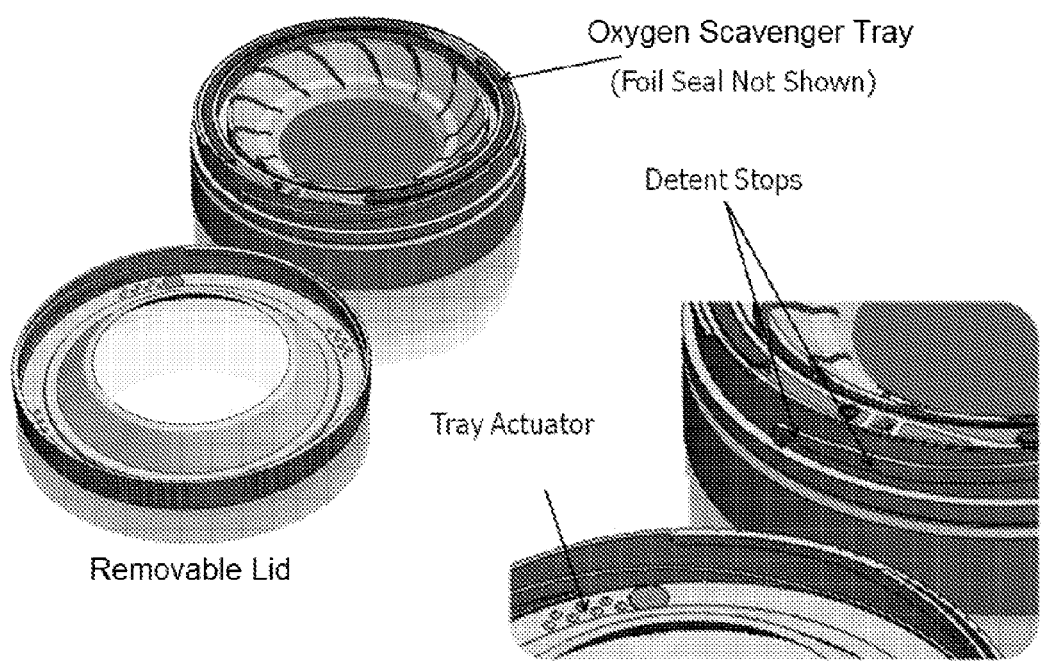
FIG. 1E is a view of a cassette with the lid removed showing a tray for an oxygen scavenger. As shown in the inset, the base includes two stops. The first allows the lid to seal the cassette without actuating the oxygen scavenger. By over rotating the lid to the second stop, a projection on the lid pierces the seal on the oxygen scavenger.
Figure 1F:
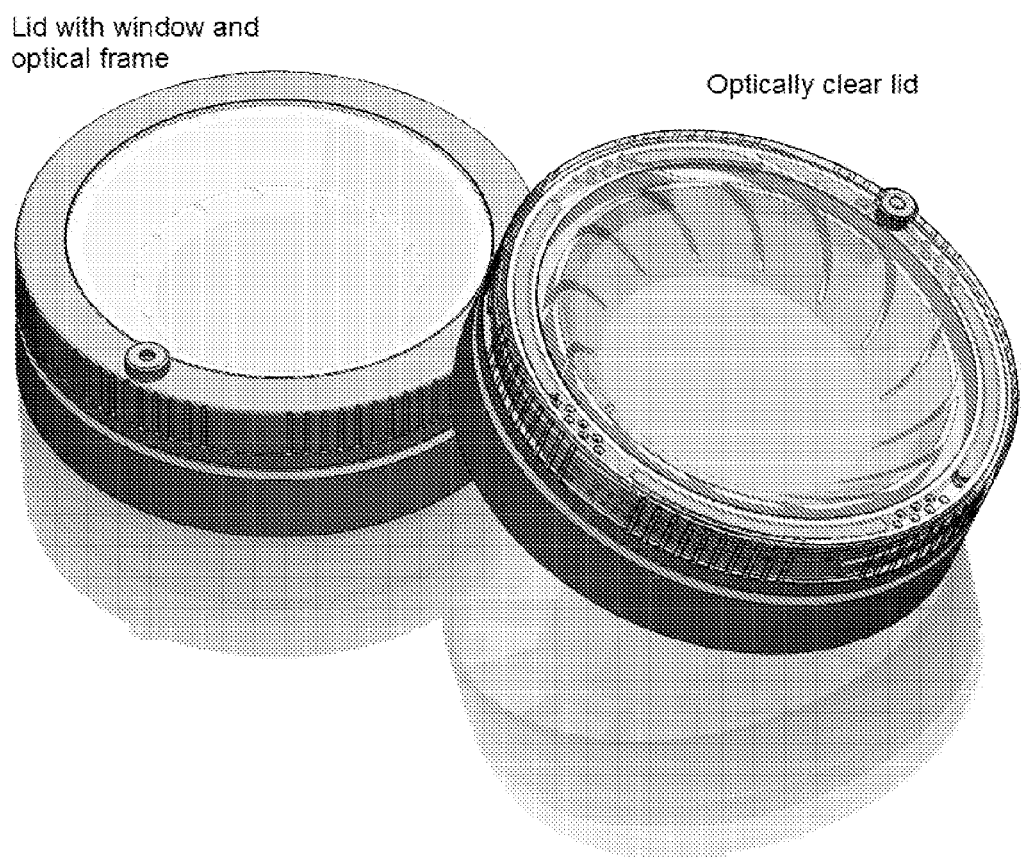
FIG. 1F is a drawing of alternative lid embodiments.

The cassette may or may not include an oxygen scavenger to render it anaerobic (e.g., FIGS. 1E, 2A, and 3A). The oxygen scavenger is typically stored within the cassette in a sealed tray or compartment, the exact location of which inside the cassette is not critical. The seal can then be disrupted once sample and media have been delivered to the cassette. Various methods for disrupting the seal are known in the art. In one embodiment, the sealed compartment is located adjacent to a projection on the lid (or base). The lid can be over rotated to cause the projection to puncture the seal on the scavenger (FIG. 1E). Actuation may also occur via a pull tab accessed through a membrane or septum located on the outside of the cassette (FIGS. 2A and 3A). Exemplary oxygen scavengers include iron oxide, glucose oxidase, or similar agents. Cassettes may also include an indicator of the interior oxygen content, located in the interior of the cassette. Suitable indicators are known in the art.

The inlet and outlet ports of the cassette are preferably self sealing, e.g., rubber septa or other self-closing valve. As is discussed below, a cassette may be provided without the self-sealing portion installed prior to use. In addition to the sample injection port and media injection port, a cassette may include a drainage port, e.g., located on the bottom or side of the base. The cassette may or may not include a pressure relief valve to control the maximum pressure inside the cassette. The volume between the lid and membrane may also be pressurizable, e.g., to prevent excess media from pooling on top of the pad or leaking through a membrane. The base may also include channels or other areas to allow for release of pressure during the introduction of media to the pad.

Preferably, a cassette is capable of being stacked in a carrier, e.g., designed to transfer and introduce a group of cassettes to an automated imaging instrument. Such automated handling of a cassette may include transport, interfacing between the cassette and carrier, positioning for automated handling, and capability for robotic transfer. The cassette may also be designed to allow for reproducible mechanical positioning, i.e., repeatedly being able to return the same cassette to same location for automated imaging.

A cassette may also include design features that facilitate alignment of multiple images. Imaging fiducial marks include a through-hole aperture over fluorescent plastic or media. Imaging fiducial marks also include printed or embossed fluorescent material on cassette. Other fiducial marks are known in the art.

Materials for manufacture of the various components of a cassette are known in the art. Such materials include plastics, polymers, metals, glass, and ceramics. In various embodiments, the cassette facilitates automated imaging of autofluorescent microbial microcolonies containing fewer than 500 cells, for example, by employing materials with fluorescence properties commensurate with such detection. An exemplary material is black K-Resin® (styrene-butadiene-copolymer; Chevron Phillips). The cassette may also employ a transparent lid that has fluorescence properties commensurate with detection of autofluorescent microbial microcolonies. An exemplary material for the lid is Zeonor® 1060R (polycycloolefin resin; Zeon Chemicals LP). Glass may also be employed. A porous membrane may also be employed that has fluorescence properties commensurate with detection of autofluorescent microbial microcolonies. Membranes may be manufactured from materials including cellulose, cellulose acetate, polystyrene, polyethylene, polycarbonate, polyethylene terephthalate, polyolefin, ethylene vinyl acetate, polypropylene, polysulfone, polytetrafluoroethylene, nylon, and silicone copolymer. The choice of membrane depends, in part, on the type of cell to be cultured (e.g., microorganisms that grow attached to a surface (anchorage-dependent), microorganisms that grow in suspension (anchorage-independent), or microorganisms that grow as attached to a surface or in suspension), degree of permeability, and rate of transfer of fluids and gases. An exemplary membrane is a black mixed cellulose ester membrane (Sartorius AG). Portions of the cassette that will not be imaged may be made of any suitable material, e.g., acrylonitrile-butadiene-styrene or styrene-acrylonitrile. An exemplary media pad is formed from sintered polyethylene (Porex Corp) that can deliver a predefined pore size and volume.

Tube Set

The invention also provides tube sets that allow for sterile connections to be made to the cassettes. A tube set includes at least one connector that mates with an inlet or outlet port of a cassette of the invention. The other end of the tube made be open, e.g., for drainage or slipping onto a nozzle or other fluid source or sink. Alternatively, the other end may contain a connector, e.g., a Luer lock, needle, or similar fitting. Tube sets may be designed to deliver fluid from one source to multiple cassettes or inlets or to remove fluid from multiple cassettes or outlets. Each tube set may be actuated by a separate pump, e.g., a peristaltic pump, or multiple tube sets may be actuated by a single pump.

Figure 9A:
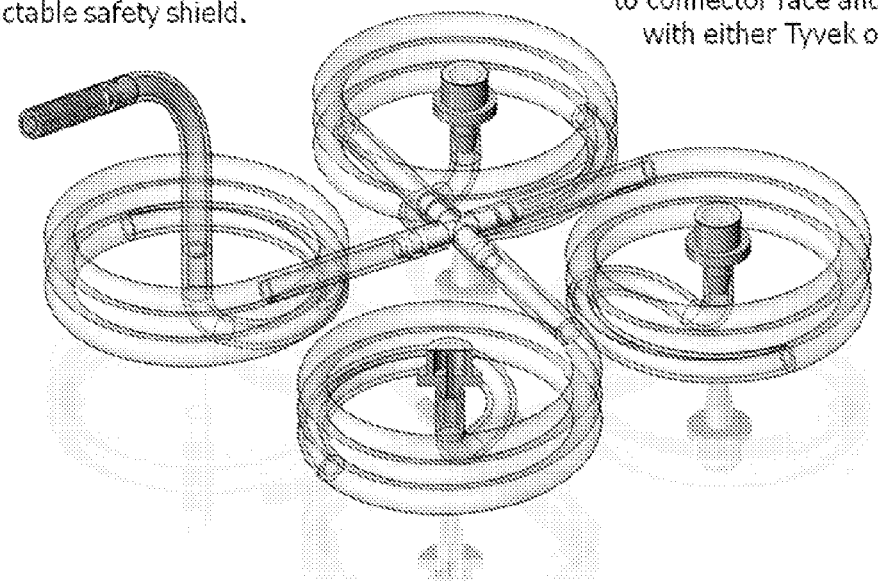
FIG. 9A is a schematic depiction of a tube set of the invention. The tube set has three connectors that mate to cassettes and a safety sheathed needle for use in sample or media delivery or waste removal.
Figure 9B:
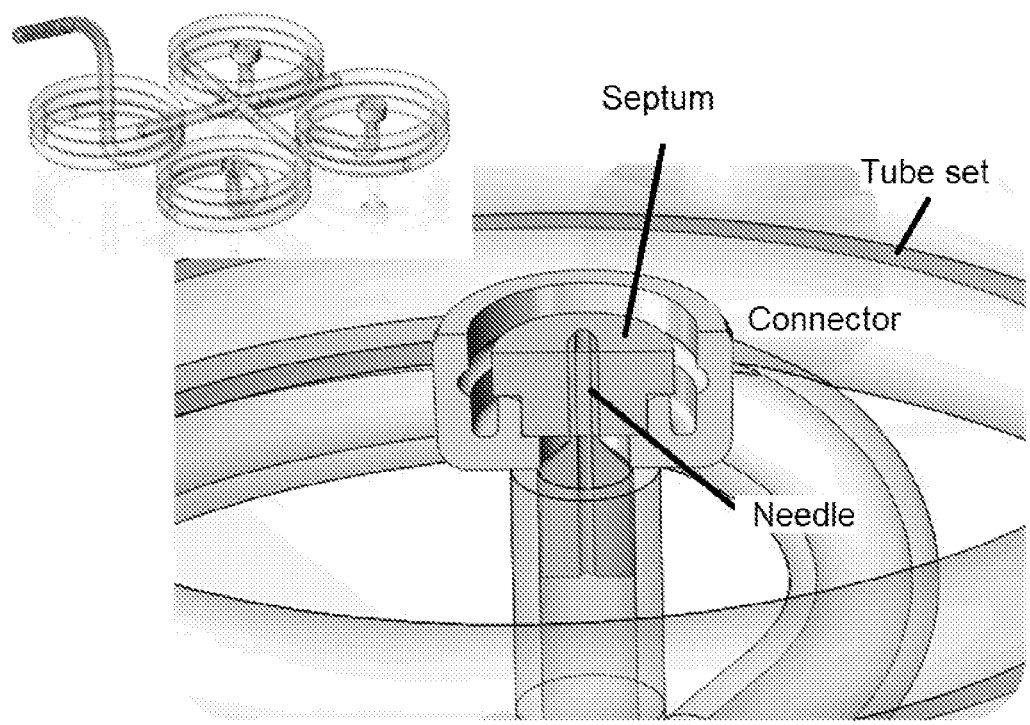
FIG. 9B is a schematic depiction of a tube set, the septum of which is retained in the cassette after use. In this example, the connector includes a groove that snaps onto a corresponding feature surrounding a port on the cassette.

In one embodiment, the connector that mates with the cassette includes a needle surrounded by a shield, so that the tip of the needle is spaced back from the edge of the shield. The shield mates to a port on the cassette, and the needle provides fluidic connectivity for delivery or removal of fluids. In a specific embodiment shown in FIGS. 9A-9B, the connector includes a septum surrounding the needle. The connector is mated to the port on the cassette and locks into place. Once fluid delivery or removal is completed, the needle and tube can be removed leaving the septum in place, thereby sealing the cassette (FIG. 9B).

Figure 10A:
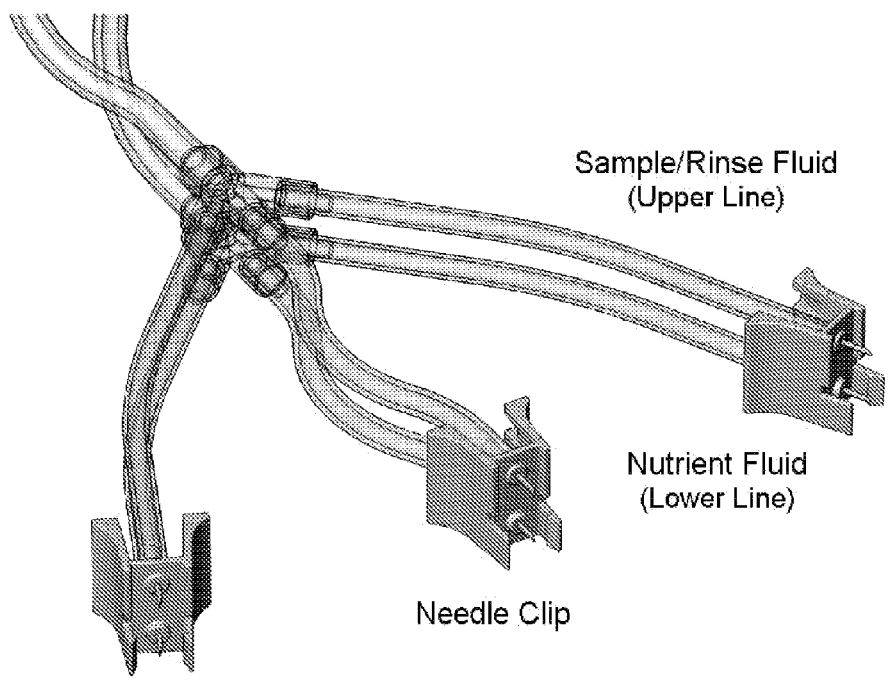
FIG. 10A is a schematic depiction of a tube set of the invention. The tube set has three connectors, e.g., branches that terminate into keyed needle clips that mate to cassettes and a safety sheathed needle (not shown) for use in sample or media delivery or waste removal. There are two fluid lines per cassette.
Figure 10B:
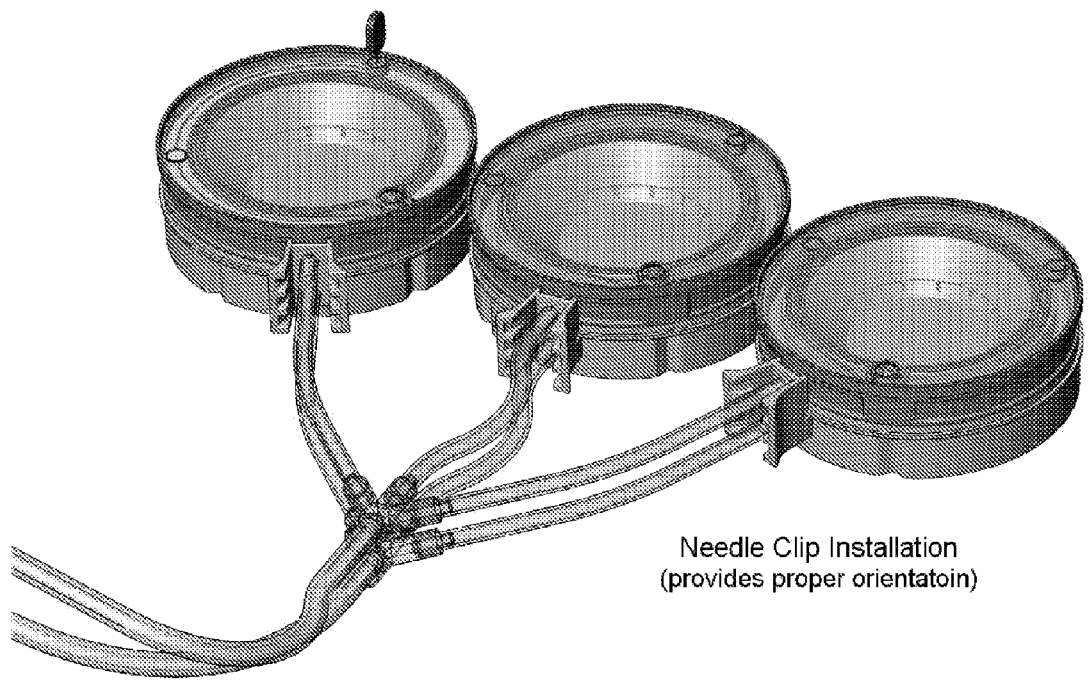
FIG. 10B is a schematic depiction of a tube set installed in the cassettes. The keyed needle clip dictates that the tube set can only be inserted in a predefined orientation.
Figure 11A:
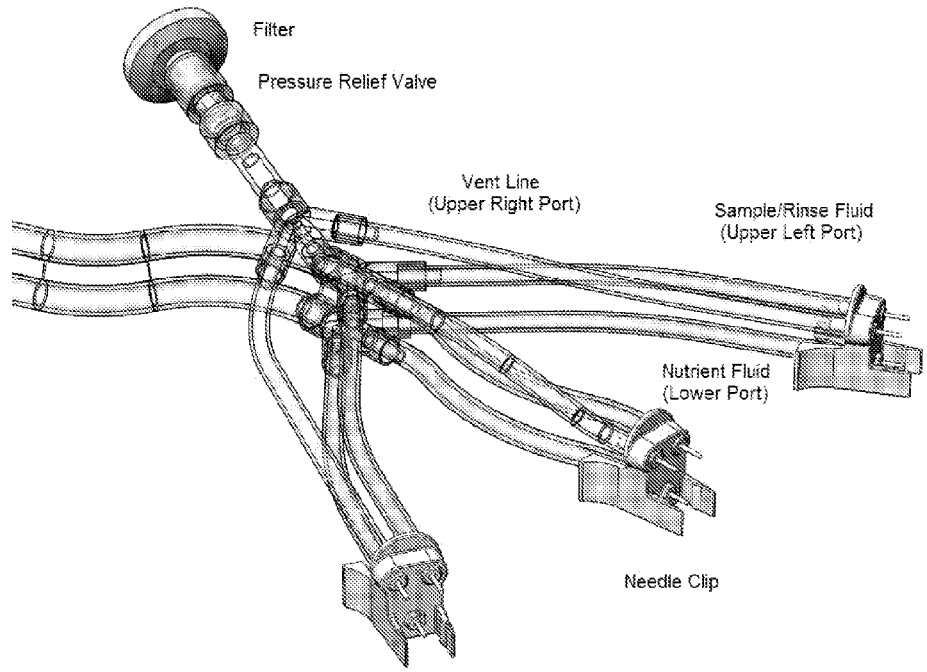
FIG. 11A is a schematic depiction of a tube set of the invention. The tube set has three connectors, e.g., branches that terminate into keyed needle clips that mate to cassettes and a safety sheathed needle (not shown) for use in sample or media delivery or waste removal. There are three fluid lines per cassette. The vent lines are shown are joining to a common valve and filter, although the tube set could employ a separate vent line for each cassette.
Figure 11B:
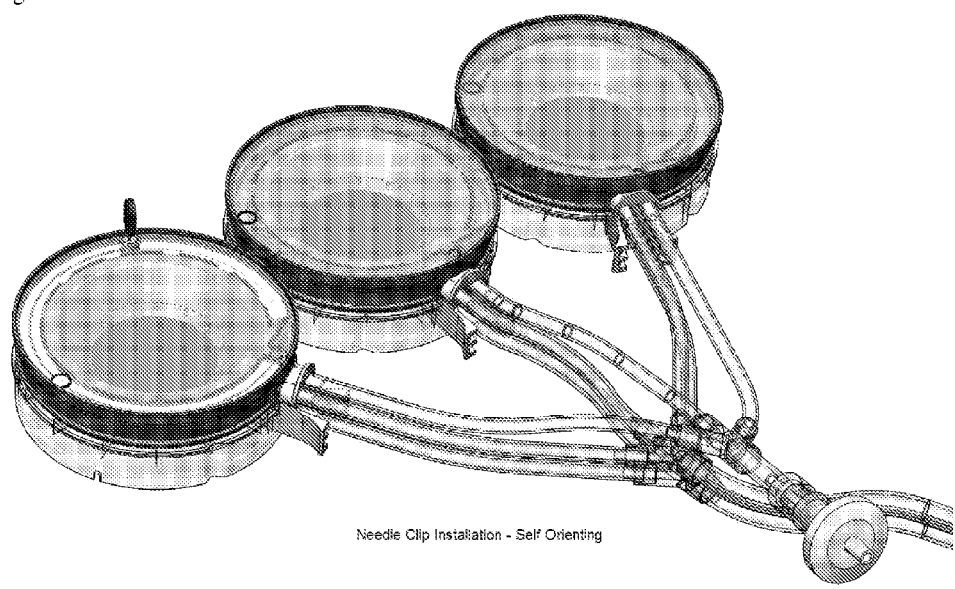
FIG. 11B is a schematic depiction of a tube set installed in the cassettes. The keyed needle clip dictates that the tube set can only be inserted in a predefined orientation.

In another embodiment shown in FIGS. 10A-10B, the connector includes two separate fluid lines, i.e., tubes, each with its own needle and configured to prevent improper installation into the cassette. In this configuration, the connector snaps into place, providing the user with positive feedback that proper insertion has been achieved (FIG. 10B). The number of fluid lines can be increased as required by the particular use. FIG. 11A-11B show an example of a tube set that includes three fluid lines, one of which provides pressure relief. The pressure relief line may include a pressure relief valve and a filter as shown. Once fluid delivery or removal is completed, the needle and tube can be removed by gently squeezing the connector, while pulling it free of the cassette.

Further access to the cassette may be made by making additional connections with needles. The connector can mate with the cassette by any suitable mechanism, e.g., screw thread, Luer lock, friction fit, and snap on fitting. One or more tubing sets, e.g., one each for sample and media delivery and waste removal, may also be packaged with one or more cassettes in a kit.

The tubing in the tube set may be made from any suitable material, such as polyethylene, polytetrafluoroethylene, and Tygon® flexible tubing. The connectors and needles may be fabricated from metals, e.g., stainless steel, plastics, ceramics, or combinations thereof.

Methods of Use

Figure 12:
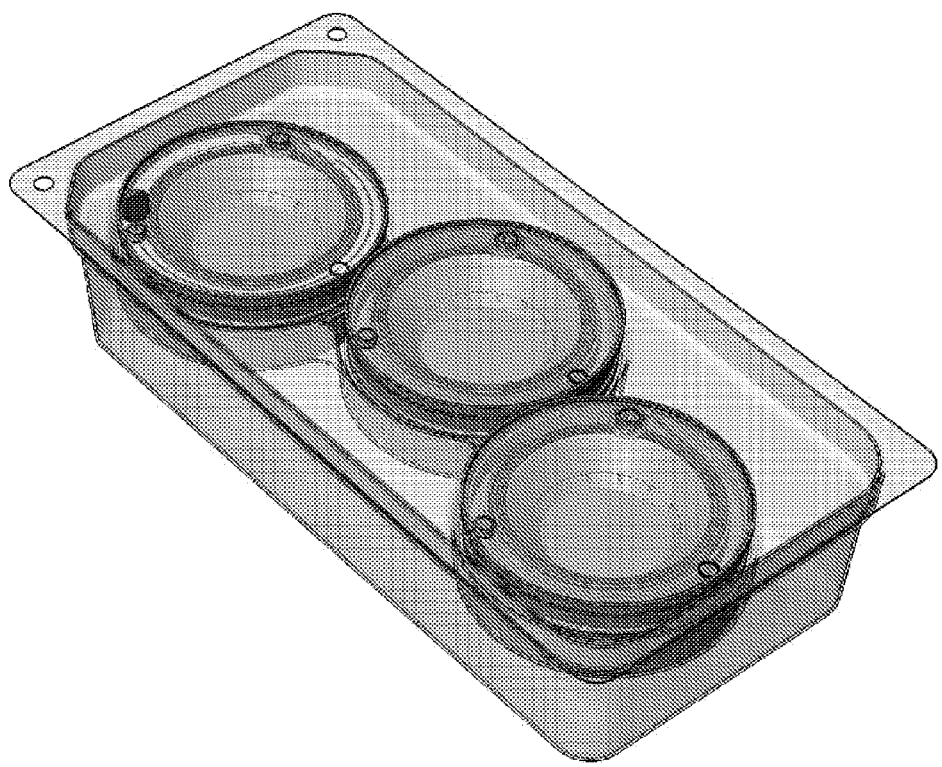
FIG. 12 illustrates one possible variation of a packaged test kit, with the breathable, access panel removed.

The cassettes and tube sets of the invention may be used in the growth or maintenance of cells, including detection, enumeration, diagnosis, and therapeutic response. Exemplary fields of use include testing liquid, air, or surface samples for microbial bioburden; testing industrial samples, sterile pharmaceutical product samples, non-sterile pharmaceutical product samples for microbial bioburden; and testing samples for anaerobic microbial bioburden. Any culturable cell type, including bacteria, cyanobacteria, protozoa, fungi, mammalian cells, plant cells, or other eukaryotic cell, may be employed in conjunction with the cassette described herein. The cassettes can be used for aerobic and anaerobic testing. The cassettes may be packaged in sterile kits or be sterilized by the end user (FIG. 12). The cassettes will typically be employed in a lab environment using either a laminar flow hood or isolation chamber.

In a typical experiment, the cassette is sterilized or provided pre-sterilized. Pre-rinse, sample media, and post rinse fluids are introduced through the sample injection port. Upon entry to the cassette, fluids will travel through the fluid distribution channel, which may include a helical stabilizing channel to calm excess turbulence, before passing across the face of the membrane. Introduction of these fluids across the face of the membrane, in a sealed chamber, may cause residual air, trapped in the cassette, to compress as the fluid column rises, resulting in a protective barrier to the underside of the optical window. Upon completion of the sampling and rinse steps, additional air may be pumped into the cassette to ensure that all fluids have been forced through the membrane and/or media pad. This may cause the chamber above the membrane to be pressurized.

Nutrient media is then pumped into the media pad via the media injection port. The media is absorbed by the media pad and provides a food source for a specified period of time, e.g., at least 7 or 14 days. Use of a membrane, e.g., with a 0.45 μm pore size, combined with pressurization of the chamber between the lid and the membrane may be used to prevent excess nutrient media from passing through the membrane.

When a drainage port is present, excess sample or media fluid can be removed from the cassette via the drainage port. Alternatively, excess sample fluid can be removed via the media injection port. A preset volume of media may also be delivered via the media injection port with displaced gas inside the cassette being vented through the sample injection port, vent port, or a pressure relief valve. Other configurations are possible.

The cassettes are preferably able to process large volumes of fluids, e.g., 2 liters of sample and 2 liters of rinse solutions. The exact amount of fluid will depend on the sample.

The cassettes may be sterilized by any suitable method. Gas sterilization, e.g., by ethylene oxide, may be performed by pressurizing the cassette with the gas, retaining the gas for a predetermined amount of time, and evacuating the gas under high vacuum.

In one embodiment, upon completion of the filtration process and nutrient transfer, the cassette is placed into an incubator, e.g., within the Growth Direct™ system, at a predefined temperature and stored while awaiting imaging. At predefined intervals the cassette is automatically retrieved and sent through an imaging station where it is subjected to a high intensity excitation light of particular wavelengths. Any microbial growth present on the membrane will naturally fluoresce in response. An image of the fluorescence is captured by means of an optical filter and a CCD camera, and fluorescent objects are recorded. Over time, subsequent images are captured, and these fluorescent objects are measured and monitored to measure growth. Those meeting the growth criteria are counted as colonies. Other fluorescent objects are characterized as debris.

The invention will now be further described with respect to certain preferred embodiments.

A cassette of the invention housed a 0.45 micron black, mixed cellulose ester filtration membrane, supported by a media pad made of sintered polyethylene beads. A sample containing mixed microorganisms was pumped through Tygon® S-50-HL tubing, via a peristaltic pump, into the sample injection port of the cassette. During sample addition, the tubing on the media injection port was sealed, and the tubing on the drainage port was open. Fluid D (a peptone-Tween 80 wash fluid) was pumped in following sample addition, followed by the addition of air to force all fluid through the membrane and to pressurize the upper chamber to about 10 psi. The sample injection port was then sealed with a clip, and the media injection port was opened. Liquid Schaedler's Blood media was added via the media injection port, and pumped into the media pad under the membrane, to replace the Fluid D rinse with growth media.

The tubing was then removed from all ports, and the ports were sealed with parafilm. The cassette was incubated at 32.5° C. The cassette was manually placed in an imager at various time intervals (with incubation between images). About 600 Watts/cm$^2$ of excitation light at 460-500 nm was provided by blue LEDs modulated by optical band-pass filters. Band pass filters of 505-550 nm allowed the emission light to be captured by a CCD camera.

For the purposes of these experiments, the lid was removed before the cassettes were placed in the imager and replaced before continued incubation. The imager captured nine tiled images at each time point, and these images were stitched together to show the complete cassette. Alignment of the cassette was by eye and manual.

Figure 13:
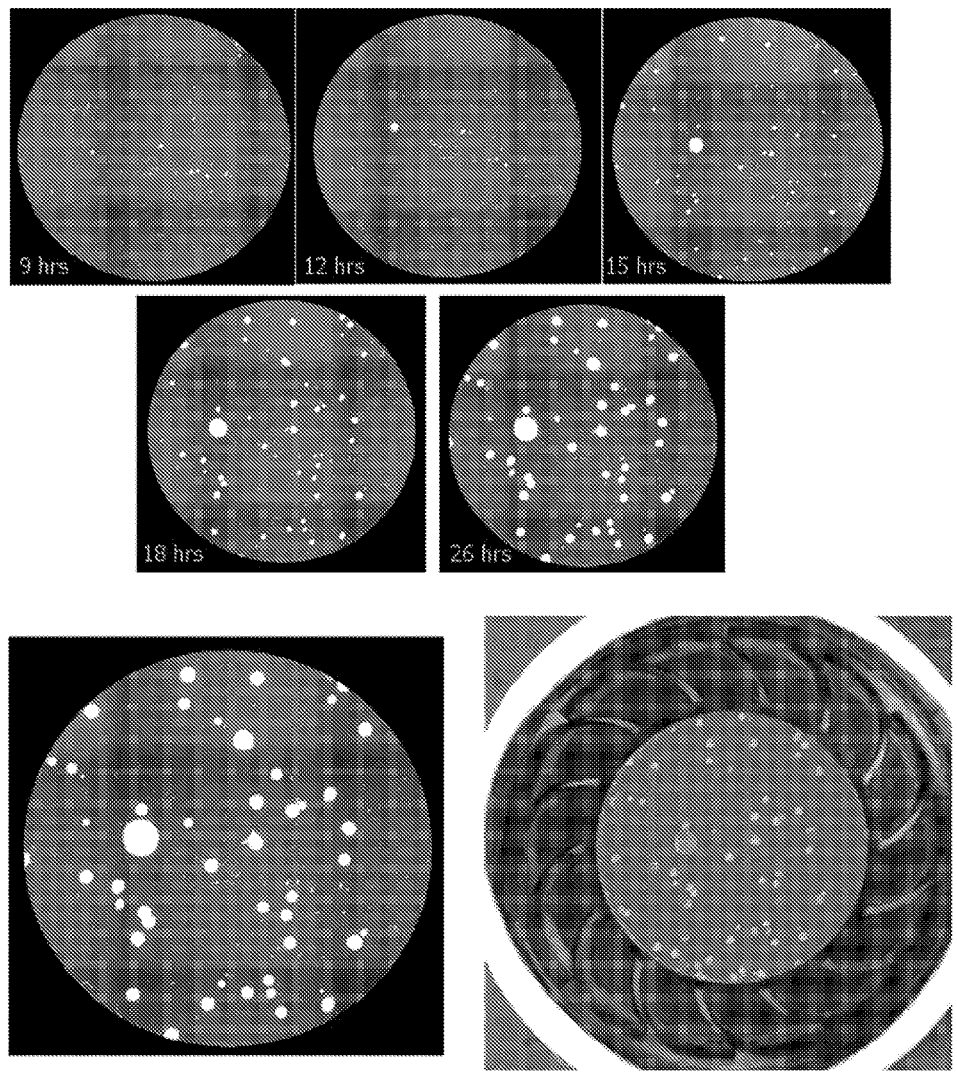
FIG. 13 is a series of micrographs showing the growth of bacteria in a cassette of the invention.

The time series in FIG. 13 shows the fluorescent images of growing colonies of microorganisms in the cassette. While there are debris particles at the start, only the fluorescence of growing microorganisms increases over time. The growing fluorescent spots can be detected as growing colonies using software algorithms and can be identified when they are still small, in part due to the resolution of the non-magnified imaging system. The last panel in FIG. 13 shows an image of the cassette at the end of the incubation period, taken in regular lighting with a digital camera. As can be seen by comparing the last two panels, there is a one-to-one correspondence between the fluorescent colonies and the colonies in the regular image.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A cell culturing device comprising a housing that contains:
   i) a lid having an optically clear window;
   ii) a fluid distribution channel;
   iii) a sample injection port fluidically connected to the fluid distribution channel;
   iv) a base that comprises a porous media pad disposed under the fluid distribution channel, wherein the porosity of the media pad is sufficient to retain cells or a membrane having a porosity sufficient to retain cells is disposed on the membrane;
   v) a media injection port fluidically connected to the media pad for introduction of liquid nutrient media to the media pad, and
   vi) a drainage port fluidically connected to the media pad; wherein sample fluid introduced through the sample infection port travels through the fluid distribution channel, the media pad, and the drainage port, whereby the sample fluid is distributed evenly to the media pad by the fluid distribution channel, and cells in the sample fluid are retained on the media pad or membrane and are viewable through the optically clear window; and wherein the lid mates to the base to form a sterile seal.

2. The device of claim 1, further comprising the membrane disposed on the media pad.

3. The device of claim 2, wherein the volume between the lid and membrane is pressurizable.

4. The device of claim 1, further comprising an oxygen scavenger sufficient to render the interior of the device anaerobic.

5. The device of claim 4, further comprising an actuator for the oxygen scavenger.

6. The device of claim 5, wherein the actuator is activated by over rotation of the lid or a pull tab.

7. The device of claim 1, further comprising a pressure-relief valve.

8. The device of claim 1, wherein the base further comprises channels that relieve pressure in the media pad when fluid is being introduced.

9. The device of claim 1, wherein the lid is removable.

10. The device of claim 1, further comprising a media distribution channel connected to the media injection port and having a plurality of outlets around the perimeter of the media pad, wherein media introduced via the media injection port is distributed evenly to the media pad via the media distribution channel.

11. The device of claim 1, further comprising an oxygen indicator.

12. The device of claim 1, wherein the fluid distribution channel comprises a helical raceway.

13. The device of claim 1, where the fluid distribution channel comprises a plurality of channels, and sample fluid introduced into the fluid distribution channel is distributed evenly to the media pad via the plurality of channels.

14. The device of claim 1, wherein the fluid distribution channel is a single channel.

15. The device of claim 14, wherein the fluid distribution channel comprises a sloped circumferential region around the media pad.

16. The device of claim 1, further comprising a cover disposed on top of the fluid distribution channel.

17. The device of claim 16, wherein the cover shapes the fluid stream to achieve uniform distribution to the media pad through a single channel.

18. The device of claim 1, further comprising a vent port for venting the interior of the device as liquids are introduced.

19. The device of claim 18, wherein the vent port is self sealing.

20. A kit for detecting cells, comprising the device of claim 1 and a first tube set comprising a tube having a connector that has a needle and mates to the sample injection port, media injection port, vent port, or drainage port.

21. The kit of claim 20, wherein the connector further comprises a septum through which the needle passes.

22. The kit of claim 21, wherein the connector mates to the sample injection port, media injection port, vent port, or drainage port and seals the port with the septum when the needle and tube are removed.

23. The kit of claim 20, further comprising second and optional third tube sets, each comprising a tube having a connector that has a needle, wherein the connectors for the second and optional third tube sets mate to one of the sample injection, media injection, vent, and drainage ports.

24. The kit of claim 23, wherein the tubes for the first, second, and optional third tube sets share a common inlet or outlet.

25. The kit of claim 20, wherein the connector comprises a clip that snaps into the device.

26. The kit of claim 20, wherein the first tube set further comprises a plurality of separate tubes for at least two of sample introduction, media introduction, drainage, and venting.

27. The kit of claim 26, wherein the connector comprises needles for each tube.

28. The kit of claim 26, wherein one of the tubes is for venting.

29. The kit of claim 26, wherein the tube for venting comprises a filter.

30. The kit of claim 26, wherein the tube for venting comprises a pressure relief valve.

\* \* \* \* \*

UNITED STATES PATENT AND TRADEMARK OFFICE
CERTIFICATE OF CORRECTION

PATENT NO. : 9,745,546 B2
APPLICATION NO. : 14/355152
DATED : August 29, 2017
INVENTOR(S) : Robert C. Aviles et al.

Page 1 of 1

It is certified that error appears in the above-identified patent and that said Letters Patent is hereby corrected as shown below:

Column 10, in Claim 1, Line 38, replace "infection" with --injection--.

Signed and Sealed this
Sixth Day of March, 2018

Andrei Iancu
*Director of the United States Patent and Trademark Office*